(12) United States Patent
Despres et al.

(10) Patent No.: US 6,673,895 B2
(45) Date of Patent: Jan. 6, 2004

(54) PRO-APOPTOTIC FRAGMENTS OF THE DENGUE VIRUS ENVELOPE GLYCOPROTEINS

(75) Inventors: Philippe Despres, La Garenne-Colombes (FR); Marie-Pierre Courageot, Paris (FR); Vincent Deubel, Vanves (FR); Adeline Catteau, Savigny sur Orge (FR)

(73) Assignee: Institut Pasteur, Paris (FR)

( * ) Notice: Subject to any disclaimer, the term of this patent is extended or adjusted under 35 U.S.C. 154(b) by 9 days.

(21) Appl. No.: 09/881,710

(22) Filed: Jun. 18, 2001

(65) Prior Publication Data

US 2002/0086403 A1 Jul. 4, 2002

Related U.S. Application Data

(60) Provisional application No. 60/212,129, filed on Jun. 16, 2000.

(51) Int. Cl.[7] .............................................. C07K 14/18
(52) U.S. Cl. ..................... 530/324; 530/326; 530/300
(58) Field of Search .................................. 530/300, 324, 530/326

(56) References Cited

U.S. PATENT DOCUMENTS 6,136,561 A * 10/2000 Ivy et al. .................. 435/69.3

OTHER PUBLICATIONS

Wang, J. et al. 2000 J. Biol. Chem. 275 (1): 507–513.*

Despres et al (Virology, vol. 196, Issue 1, Sep. 1993, pp. 209–219.*

Philippe Despres et al "Apoptosis in the Mouse Central Nervous System in Response to Infection With Mouse–Neurovirulent Dengue Viruses" Journal of Virology, Jan. 1998, pp. 823–829.

AM Pietersen et al "Specific Tumor–Cell Killing With Adenovirus Vectors Containing The Apoptin Gene", Gene Therapy (1999) 6, pp. 882–892.

Philippe Despres "Human Isolates of Dengue Type 1 Virus Induce Apoptosis in Mouse Neuroblastoma Cells", Journal of Virology, Jun. 1996, pp. 4090–4096.

M. H. M. Noteborn Apoptin®–Induced Apoptisis: A Review, Apoptosis 4: pp. 317–319 (1999).

* cited by examiner

Primary Examiner—Mary E. Mosher
Assistant Examiner—Misook Yu
(74) Attorney, Agent, or Firm—Oblon, Spivak, McClelland, Maier & Neustadt, P.C.

(57) ABSTRACT

The present invention relates to pro-apoptotic fragments of the Dengue virus pRM and E glycoproteins, methods of screening for molecules capable of inducing apoptosis and methods of inducing apoptosis in a cell.

7 Claims, 19 Drawing Sheets

Figure 1A:
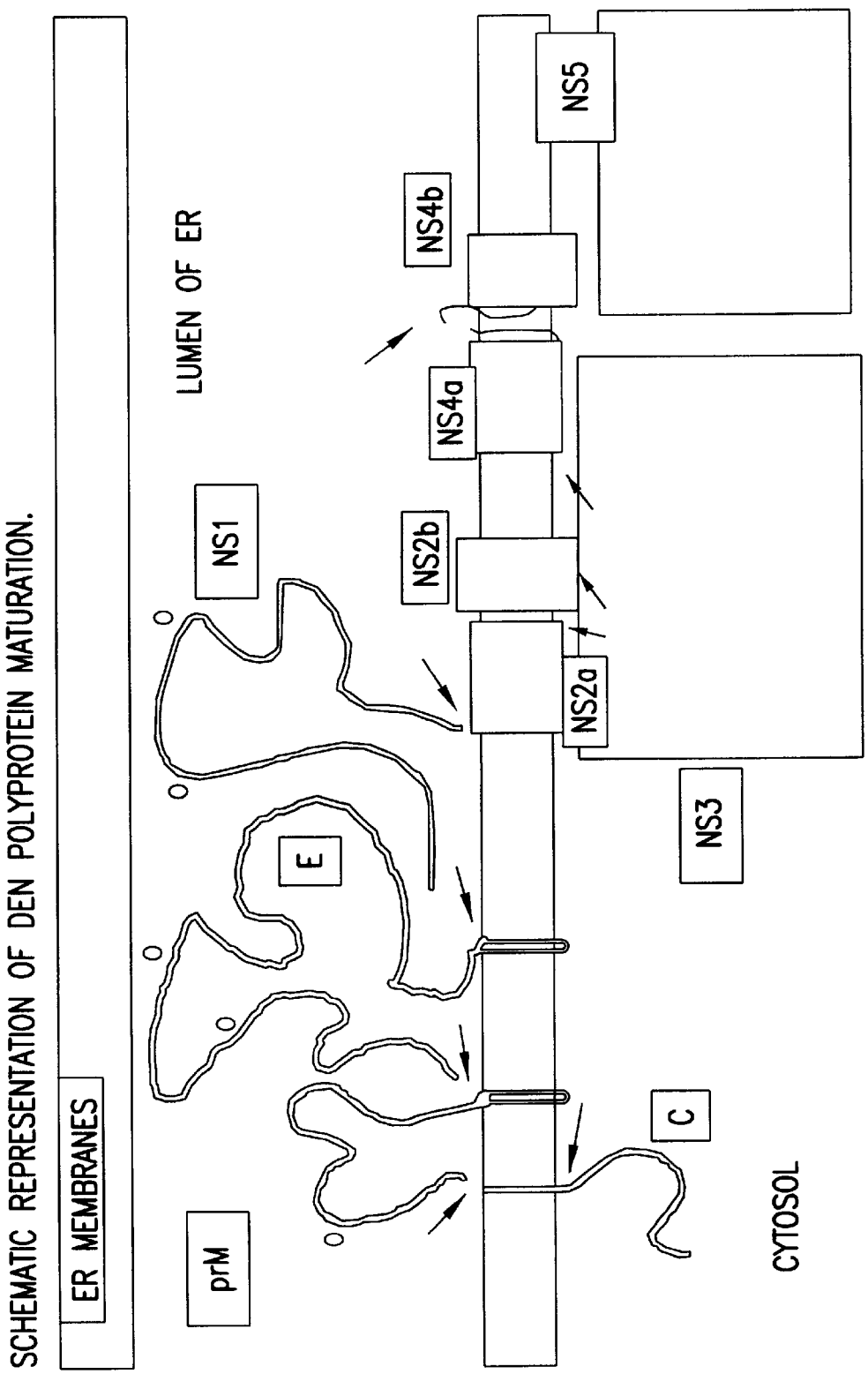

NEURO 2a CELLS EXPRESSING THE [95-114]EGFP[206-245] FUSION PROTEIN
IN APOPTOTIC STATE (POD-TUNEL)

HepG2 CELLS TRANSFECTED DURING 20 HOURS:
QUANTIFICATION OF FREE OLIGONUCLEOSOMES BY ELISA

FIG. 6

Sequence of the plasmide p[95-144]EGFP[206-245]

Sequence in the 5' of the gene EGFP of the plasmide pEGFP-N1 (Clontech, #6085-1, Gene bank accession #U55762)

```
      591       601       611       621       631       641       651       661       671    EGFP→
5' G CTA GCG CTA CCG GAC TCA GAT CTC GAG CTC AAG CTT CGA ATT CTG CAG TCC ACG GTA CCC GCC CGG GAT CCA CCG GTC GCC ACC ATG
      Nhe I                                                                            Sma I              Sma I
```

Sequence of the virus Den-1 strain BR/90 in the 5' of the gene of

FIG. 7

SIMILARITY AND IDENTITY BETWEEN DEN VIRUS AND WN VIRUS

M (West-Nile virus strain IS-98 ST1)
215                                                           255
RSLTVQTHGESTLANKKGAWMDSTKATRYLVKTESWILRNP
SVALAPHVGLGLETRTETWMSSEGAWKQIQKVETWALRHP
206                                                       245
M (DEN-1 virus strain FGA/89)
32% identity, 66% similarity Protein M sequences of strains NY99-flamingo382-99 (Genpept access : AF196835 1) and HNY1999 (Genpept access : AF202541 1) and isolate 2741 (Genpeptnew access : AF206518 1) of West-Nile virus are identical to that of WN strain IS-98 ST1.

FIG.9

Similarity and Identity

Sequence of the protein M of the virus DEN-1/CD72
M (virus DEN-1, strain FGA/89)
S V A L A P H V G L G L E T R T E T W M S - S E G A W K Q I Q K V E T W A L R H
S P A L A D K A G V G S E Q P T A T W S S V K S S A L R Q I P R C P T V C L Q N
CD72 (aa 56-95)                                    40% identity
Swiss Prot Library under Accession NosP21855

Peptide 217-242 of the protein M of the virus DEN-1/Bax
L E T R T E T W M S S E G A W K Q I Q K         DEN-1
L R E R L L G W I Q D Q G G W D G L L S         BH2 (Bax)
identity 25%, similarity 70%

GenBank Data Library under Accession NosQ 07812

Sequence 217-242 of the protein M from Flavivirus

| | |
|---|---|
| L E T R T E T W M S S E G A W K Q I Q K | DEN-1 |
| L E T R T E T W M S S E G A W K H A Q R | DEN-2 |
| L D T R T Q T W M S A E G A W R Q V E K | DEN-3 |
| L E T R A E T W M S S E G A W K H A Q R | DEN-4 |
| L S N K K G A W M D S T K A T R Y L V K | KUN |
| L V N K K E A W L D S T K A T R Y L M K | JE |
| L V N K K D A W L D S T K A T R Y L T K | MVE |
| L A N K K G A W M D S T K A T R Y L V K | WN |
| L A T K N T P W L D T V K T T K Y L T K | SLE |
| L K T R Q E K W M T G R M G E R Q L Q K | YF |
| L T G R G H K W L E G D S L R T H L T R | TBE |
| L T G R G H Q W L E G E A V K A H L T R | LANGAT |
| M V G T G H A W L K G D N I R D H V T R | POW |

| | | |
|---|---|---|
| DEN-1 | GenBank Data Library under Accession Nos | AF 226687 |
| DEN-2 | GenBank Data Library under Accession Nos | M 20558 |
| DEN-3 | GenBank Data Library under Accession Nos | M 93130 |
| DEN-4 | GenBank Data Library under Accession Nos | M 14931 |
| KUN | GenBank Data Library under Accession Nos | D 00246 |
| JE | GenBank Data Library under Accession Nos | U 14163 |
| MVE | GenBank Data Library under Accession Nos | GNWVMV |
| WN | GenBank Data Library under Accession Nos | AF 196835 |
| SLE | GenBank Data Library under Accession Nos | AF M16614 |
| YF | GenBank Data Library under Accession Nos | K 02747 |
| TBE | GenBank Data Library under Accession Nos | X 07755 |
| LANGAT | GenBank Data Library under Accession Nos | M 73805 et M86650 |
| POW | GenBank Data Library under Accession Nos | L 06436 |

FIG.10

Sequence of the plasmide p[95-114]EGFP[206-245]DEN-2

Sequence in the 5' of the gene EGFP of the plasmide pEGFP-N1 (Clontech, #6085-1, Gene bank accession #U55762)

591 601 611 621 631 641 651 661 671 EGFP →

5' G CTA GCG CTA CCG GAC TCA GAT CTC GAG CTC AAG CTT CGA ATT CTG CAG TCG ACG GTA CCG CGG GCC CGG GAT CCA CCG GTC GCC ACC ATG

Nhe I Sma I

Sequence of the virus DEN-1 strain BR/90 in the 5' of the gene of 1'EGFP sequence DEN-1 →

M N R R K R S V T M L L M L L P T A L A R E P P V A T M

5' G CTA GCA ATG AAC AGG AGG AAA AGA TCC GTG ACC ATG CTC CTC ATG CTG CTG CCC ACA GCC CTG GCC CGG GAT CCA CCG GTC GCC ACC ATG

Nhe I Sma I

Sequence in the 3' of the gene EGFP of the plasmide pEGFP-N1

1380 1390 1400 1410

L A M E E L Y N ochre

5' CTC GGC ATG GAC GAG CTG TAC AAG TAA AGC GGC CGC ACT CTA

BsrG I Not I

Sequence of the virus DEN-2 strain JAM in the 3' of the gene of 1'EGFP

P H V G M G L E T R T E T W M S S E G A W K I I V Q R I E T W 1380 1390

L A M E E L Y R S V A L V I L R H P opal

5' CTC GGC ATG GAC GAG CTG TAC AGA TCA GTG GCA CTC GTT.......ATC TTG AGA CAT CCA TGA GCGGCCGCGACTC

BsrG I Not I

FIG.11

¹SVALVPHVGMGLETRTETWMSSEGAWKHAQRIETWILRHP⁴⁰

| Fragment | EGFP-POSITIVE HeLa CELLS IN APOPTOTIC STATE (%) | FLUORESCENT MASSES |
|---|---|---|
| 1-40 | 24 ± 2 | + |
| 10-40 | 25 ± 0.5 | + |
| 1-30 | 17 ± 0.5 | − |
| 20-40 | 12 ± 1 | + |
| 30-40 | 5 | + |
| 1-20 | <5 | − |
| 10-30 | <5 | − |

FIG.12

PRO-APOPTOTIC FRAGMENTS OF THE DENGUE VIRUS ENVELOPE GLYCOPROTEINS

CROSS-REFERENCE TO RELATED APPLICATION

The present application claims priority to U.S. Provisional Application Ser. No. 60/212,129 filed Jun. 16, 2000, the entire contents of which are incorporated herein by reference.

FIELD OF THE INVENTION

The present invention relates to fragments of the Dengue virus glycoproteins prM and E which induce apoptosis and can be used as a therapeutic agent against Flavivirus infection and cancer.

BACKGROUND OF THE INVENTION

Dengue (DEN) is the major arbovirus transmissible to humans in most tropical and subtropical zones. At present neither treatments nor vaccines are available to counter the disease. The infectious agent is the DEN virus, a member of the Flaviviridae family, which includes viruses that are highly pathogenic for humans, such as yellow fever virus, West Nile virus, tick-borne encephalitis viruses, Japanese encephalitis virus and hepatitis C and G viruses. The DEN virus is an enveloped virus of 40 to 60 nm diameter, whose genome is a single-stranded RNA molecule of positive polarity containing about 11000 nucleotides. The viral genome is associated with the C capsid protein to form the nucleocapsid (NC). The NC is surrounded with an envelope consisting of a double lipid layer issued from membranes of the endoplasmic reticulum (ER), in which the envelope glycoprotein E and the membrane protein M are anchored. The glycoproteins prM (precursor of protein M) and E of the viral envelope are translocated in the lumen of the ER and remain anchored to the ER membranes by their transmembrane domains (TMD) (FIG. 1A). The first stage of viral morphogenesis is non-covalent association of prM and E as a heterodimeric complex within the ER. The viral particle is probably assembled by a budding process in the ER. The provirions are carried in the vesicles, which transport them toward the plasmic membrane by passing through the Golgi complex. Cleavage of prM to M by proteases of the furine type in the trans-Golgi complex permits the virions to become fully infectious.

In vivo infection of murine neurons and of human hepatocytes by the DEN virus induces cell death by apoptosis. In vitro, the induction of the apoptotic process by infection with the DEN-1 and DEN-2 viruses have been reproduced in murine neuroblastoma cells (Neuro 2a) and in human hepatoma cells (HepG2), in human Hela cells, CHO, 293T and the primate cell line VERO. We have formulated the hypothesis that accumulation of glycoproteins of the envelope of the DEN virus in the ER would lead to a stress which induces apoptosis. In the case of human hepatomas, this stress would lead to activation of the transcription factor NF-κB, which would control the expression of pro-apoptotic genes.

Apoptosis, or programmed cell death (PCD) is a type of cell death that is fundamentally distinct from degenerative death or necrosis. It is an active process of gene-directed cellular self-destruction which in some instances, serves a biologically meaningful homeostatic function. This can be contrasted to necrosis which is cell death occurring as the result of severe injurious changes in the environment of infected cells. For a general review of apoptosis, see Tomei, L. D. and Cope, F. O. Apoptosis: The Molecular Basis of Cell Death (1991) Cold Spring Harbor Press, N.Y.; Tomei, L. D. and Cope, F. O. Apoptosis II: The Molecular Basis of Apoptosis in Disease (1994) Cold Spring Harbor Press, N.Y.; and Duvall and Wyllie (1986) Immun. Today 7(4): 115–119.

Morphologically, apoptosis is characterized by the rapid condensation of the cell with preservation of membranes. Synchronistically with the compaction of chromatin, several biochemical changes occur in the cell. Nuclear DNA is cleaved at the linker regions between nucleosomes to produce fragments which are easily demonstrated by agarose gel electrophoresis wherein a characteristic ladder develops.

Apoptosis has been linked to many biological processes, including embryogenesis, development of the immune system, elimination of virus-infected cells, and the maintenance of tissue homeostasis. Apoptosis also occurs as a result of human immunodeficiency virus (HIV) infection of $CD4.sup.+$ T lymphocytes (T cells). Indeed, one of the major characteristics of AIDS is the gradual depletion of $CD4.sup.+$ T lymphocytes during the development of the disease. Several mechanisms, including apoptosis, have been suggested to be responsible for the CD4 depletion. It is speculated that apoptotic mechanisms might be mediated either directly or by the virus replication as a consequence of the HIV envelope gene expression, or indirectly by priming uninfected cells to apoptosis when triggered by different agents.

Reference is made to standard textbooks of molecular biology that contain definitions and methods and means for carrying out basic techniques, encompassed by the present invention. See, for example, Maniatis et al., Molecular Cloning: A Laboratory Manual, Cold Spring Harbor Laboratory, New York (1982) and Sambrook et al., Molecular Cloning: A Laboratory Manual, Cold Spring Harbor Laboratory, New York (1989) and the various references cited therein.

Figure 1B:
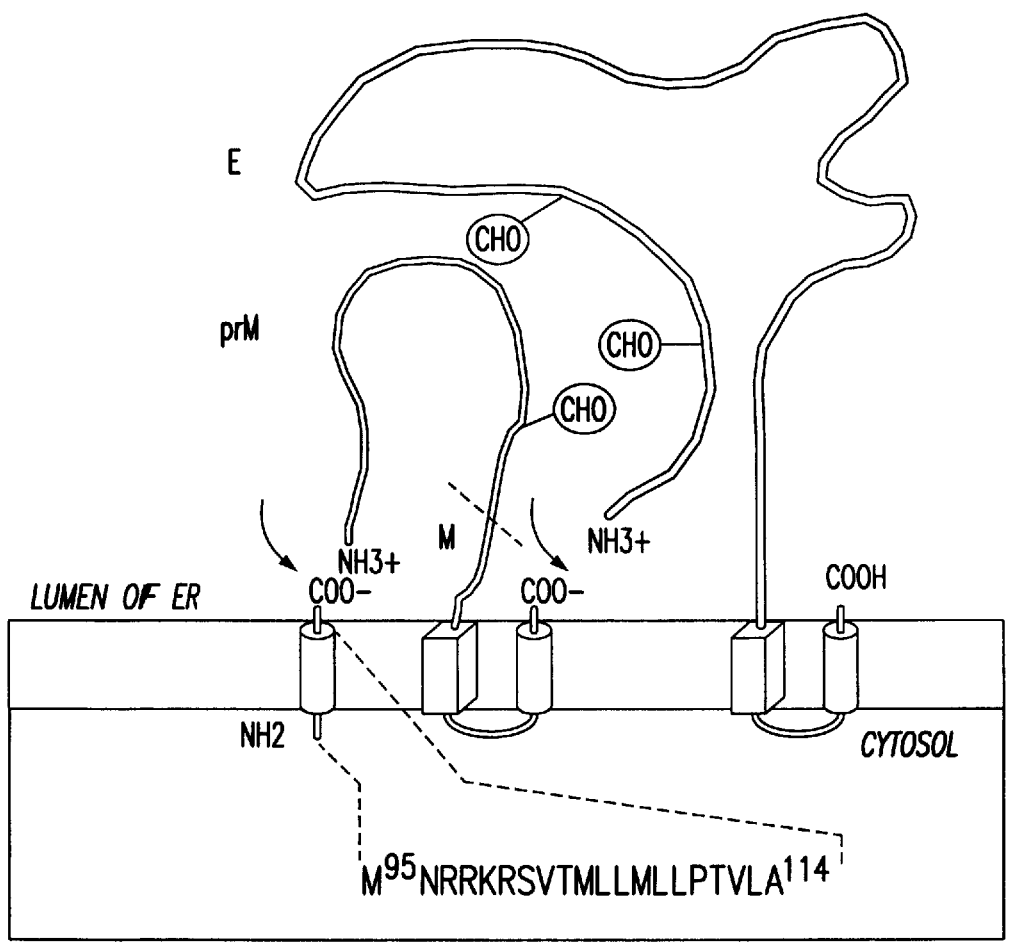

We have studied what viral morphogenesis in the cytotoxity of the DEN virus might mean for the murine neuronal cell. The first stages of assembly of the viral particle, in other words the heterodimeric association of the envelope glycoproteins prM and E in the lumen of the ER, were characterized in Neuro 2a cells infected by the FGA/89 strain of the DEN-1 virus (the viral sequence numbering begins at $Met_1$ of the DEN polyprotein, FIG. 1B), or by starting from the established line N2aprM+E (a stable clone of the Neuro 2a cells), which contains cDNA coding for the two viral glycoproteins under the control of an inducible promoter (ecdysone expression system).

Figure 2A:
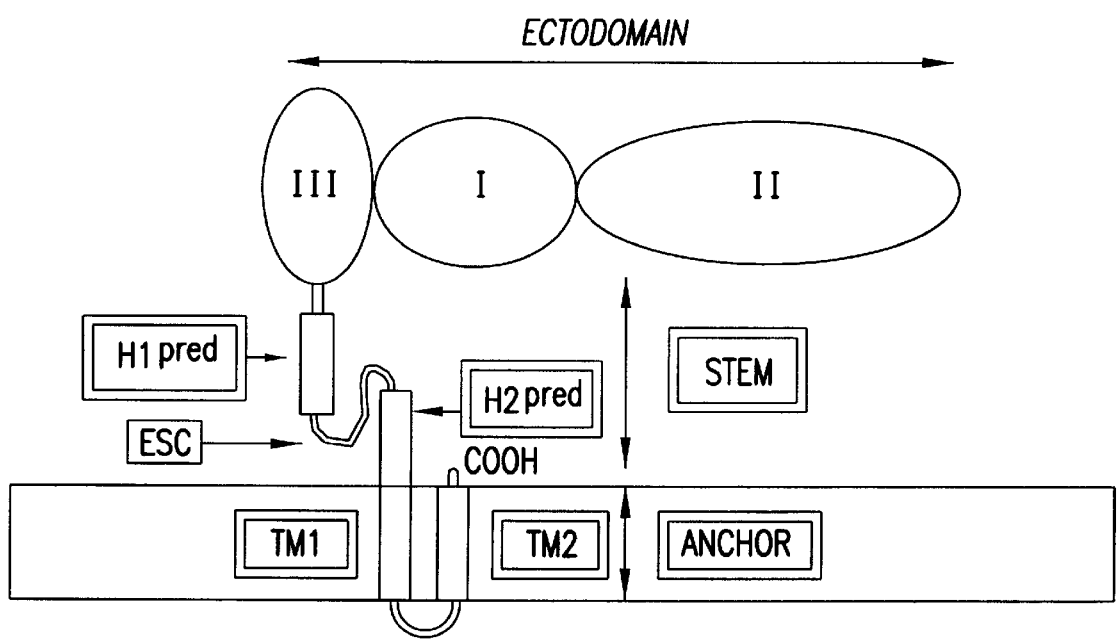
Figure 2B:
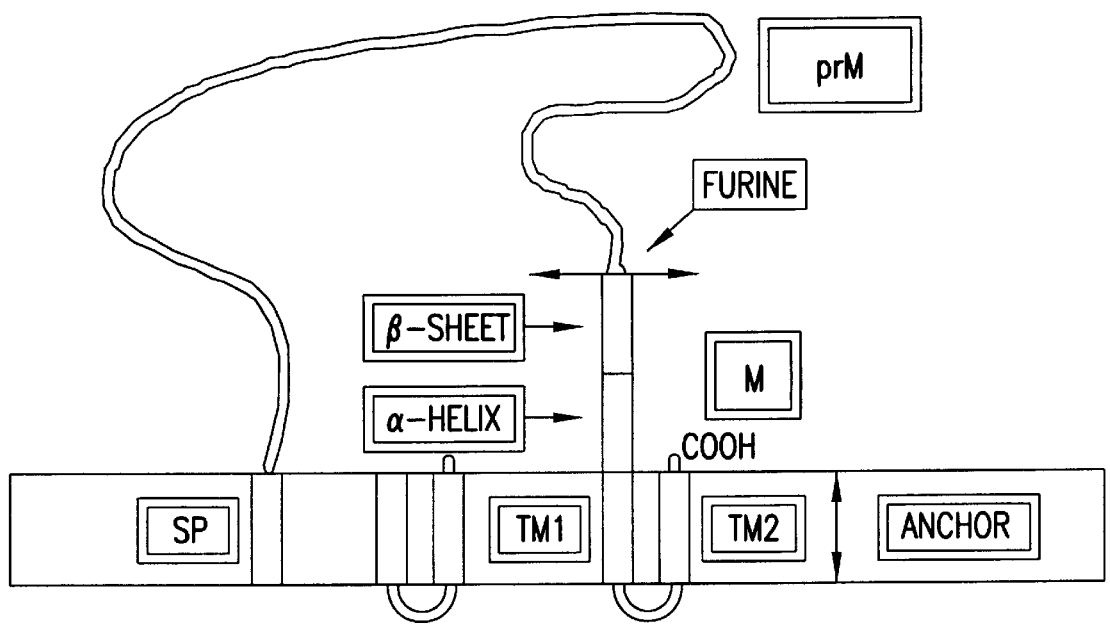

The expression of the recombinant glycoproteins prM and E in N2aprM+E cells causes cell death by apoptosis after 35 hours of induction. We attempted to identify the proapoptotic sequences in glycoproteins prM and E. The three-dimensional structure of protein E ectodomain of flaviviruses revealed the existence of three domains. Two predicted α-helices (FGA/89 polyprotein residues 680 to 692, 710 to 727) positioned between the ectodomain (390 amino acids) and the TMD (FGA/89 polyprotein residues 737 to 775) of protein E (FIG. 2A). Little information is available on the spatial structure of protein prM. Protein M (FGA/89 polyprotein residues 206 to 280) produced by posttranslational cleavage of the glycoprotein prM in the trans Golgi network, is a non-glycosylated polypeptide of 75 amino acids composed of a predicted β-sheet (FGA/89 polyprotein residues 206 to 224), a predicted α-helix (FGA/89 polyprotein residues 224 to 245) and two TMDs (FGA/89 polyprotein residues 246 to 280) (FIG. 2B).

SUMMARY OF THE INVENTION

An object of the present invention is to provide a polypeptides from the Dengue virus glycoproteins which induces apoptosis.

Another object of the present invention is to provide a polynucleotide which encodes the polypeptide.

Another object of the present invention is a method of inducing apoptosis in a cell comprising administering the polypeptide to a cell.

Another object of the present invention is a method of screening for polypeptides which are capable of inducing apoptosis.

Another object of the present invention is a method of screening for molecules capable inhibiting apoptosis induced by the polypeptide from the Dengue virus glycoproteins which induces apoptosis.

Another object of the present invention is pro-apoptotic sequences in glycoproteins prM (DEN polyprotein residues 115 to 280) and E (DEN polyprotein residues 281 to 775) of the FGA/89 strain of DEN-1 virus (Genbank Data Library under accession AF226687).

Another object of the present invention is pro-apoptotic sequences of the strain DEN-2 virus Jamaica.

The invention also relates to monoclonal antibodies raised against DEN-1 and DEN-2 virus M proteins and their utilization for the prevention of disease and diagnostic purposes.

BRIEF DESCRIPTION OF THE DRAWINGS

FIG. 1: A. Schematic representation of DEN polyprotein maturation. B. Schematic representation of recombinant prM (SEQ ID NO: 10)and E proteins.

FIG. 2: A. Schematic representation of E protein structure. B. Schematic representation of prM protein structure.

FIG. 3: The C-terminal 20 amino acids of the BR/90 C protein (residues 95 to 114) function as a sequence signal to direct the translocation of prM into the lumen of the ER. The two alanine residues at the position C-112 and C-114 provide a functional signal peptidase site. The C residues 95 to 114 (residues 2–20 of SEQ ID NO:1) followed 6 vector-specified amino-acid to the N-terminus of EGFP encoded by the plasmid pFGFP-NI (Clontech, # 6085-1) produce the [95–114]EGFP fusion protein. The regions of the FGA/89 polyprotein corresponding either the M protein (or its deletion variants) or the predicted α-helix and TMDs of the E protein were fused to the C-terminus of the [95–114]EGFP fusion construct.

FIG. 4: A. Two sets of Neuro 2a cells are transfected during 25 hours and stained by POD-TUNEL method. The (95–114]EGFP fusion proteins are indicated on the y axis and the number of TUNEL$^+$ cells per 50,000 cells is indicated on the x axis. Data were compared to the result of [95–114]EGFP[206–280] data with the Fisher and Yates t test. Only significant data ($P<0.05$) are indicated. B. Three sets of Neuro 2a cells were transfected during 20 hours. The free oligonucleosomes are quantified by ELISA method. Data were compared to the result of [95–114]EGFP [206–280] data with the Fisher and Yates t test. Only significant data ($P<0.05$) are indicated. C. Two sets of Neuro 2a cells expressed the [95–114]EGFP[206–245] fusion construct during different times of transfection. Apoptotic cells are stained by POD-TUNEL method. D. Neuro 2a cells expressing the [95–114]EGFP[206–280], the [95–114] EGFP[206–245] or the EGFP[206–245] during 25 hours are stained Cy™ 3-TUNEL and analyzed by confocal method.

FIG. 5: A. Three sets of HepG2 cells were transfected during 20 hours. The free oligonucleosomes are quantified by ELISA method. Data were compared to the result of [95114]EGFP[673–727] data with the Fisher and Yates t test. Only significant data ($P<0.05$) are indicated. B. HepG2 cells expressing the [95–114]EGFP[206–280], the [95–114] EGFP[206–245] or the EGFP[206–245] during 25 hours are stained by Cy™ 3-TUNEL and analyzed by confocal method.

FIG. 6: The sequence of the plasmid p[95–114]EGFP [206–245] encompassing the DEN-1 virus strain BR/90 encompassing the C protein residues 95 to 114 upstream of the EGFP gene, and the sequence of the DEN-1 virus strain FGA/89 encoding the M protein residues 206 to 245 downstream of the EGFP gene, in the pEGFP-N1 (SEQ ID NO:1-fusion protein; SEQ ID NOS:4, 5, 6, and 7-nucleotide sequences; SEQ ID NO:8-3' sequence of pEGFP-N1).

FIG. 7: The sequence of the plasmid p[95–114][211–245] encompassing the DEN-1 virus strain BR/90 encoding the C protein residues 95 to 114 (amino acids 1–21 of SEQ ID NO:1; nucleotides 1–68 of SEQ ID NO:5) fused to the N-terminus of the sequence of the DEN-1 virus strain FGA/89 encoding the M protein residues 211 to 245 (amino acids 42–77 of SEQ ID NO:1; nucleotides 44–74 of SEQ ID NO:7 in the pEGFP-N1 (SEQ ID NOS:4 and 6; SEQ ID NO:9).

FIG. 8: HepG2 and Neuro 2a cells expressing the [95–114][211–280] during 25 hours are stained by Cy™ 3-TUNEL and analyzed by confocal method.

FIG. 9: The regions of IS-98 ST1 strain of West Nile (WN) virus encoding the M Protein residues 215 to 255 are fused to the C-terminus of the [95–114]EGFP fusion construct. The sequence identity and similarity of M protein of DEN-1 virus strain FGA/89 (amino acids 37–77 of SEQ ID NO:1) and WN virus strain IS-98 ST1 (SEQ ID NO:27) are indicated.

FIG. 10: Sequence similarity and identity of M protein between FGA/89 strain of DEN-virus and the residues 56 to 95 of CD72 protein (SEQ ID NOS:12 and 13), and the domain of Bax protein (amino acids 12–32 of SEQ ID NO:12 and SEQ ID NO:14), and the other flaviviruses (amino acids 12–32 of SEQ ID NO:12 and SEQ ID NOS:15–26).

FIG. 11: Sequence of plasmid p[95–14]EFGP[206–245] DEN-2 (amino acids 1–29 of SEQ ID NO:1, SEQ ID NOS:9 and 11; SEQ ID NOS:3, 4, 5, 6 and 7).

FIG. 12: Deletion mutants of ectoM DEN-2. (SEQ ID NO:29)

FIG. 13: Recombinant lentiviral vectors.

FIG. 14: Cell-death inducing activity of trip ectoM DEN-1.

FIG. 15: Cytotoxicity of ectoM molecules.

DETAILED DESCRIPTION OF THE INVENTION

The 40 amino-acid long sequence of the dengue virus M protein (DEN-1 virus strain FGA/89, residues 206–245) fused to the C-terminus of the [95–114]EGFP fusion product to produce [95–114]EGFP [206–245] fusion protein is shown in FIG. 6 (SEQ ID NO:1).

The inventors determined that the sequences (40 amino acids) of the DEN-1 and DEN-2 M proteins are 83% identical as shown in the following alignment (SEQ ID NOS: 28 AND 29):

```
SVALAPHVGLGLETRTETWMSSEGAWKQIQKVETWALRHP    DEN-1 M ectodomain

----V----M----------------HA-RI---I----    DEN-2 M ectodomain
```

The amino acid sequence of the DEN-2 M polypeptide is shown in FIG. 11 and is SEQ ID NO:3) Polynucleotides encoding, the amino acid sequence can be determined from the standard genetic code disclosed for example in *Molecular Cloning: A Laboratory Manual*, Second Edition, Sambrook, Fritsch, and Maniatis, Cold Spring Harbor Laboratory Press, 1989.

The amino acid sequence of Den-1-C amino acids 95–114 is shown in FIG. 1B (SEQ ID NO:2).

The plasmid p[95–114]EGFP[206–245] has been deposited at the Collection Nationale de Cultures de Microorganismes, 25 Rue de Docteur Roux, F-75724 Paris Cedex 15 on Jan. 21, 2000 under the number I-2380. The plasmid p[95–114][211–245] has been deposited at the Collection National de Cultures de Microrganismes, 25 Rue de Docteur Roux F-75724 Paris, Cedex 15 on May 10, 2000 under the accession number I-2475.

To produce p[95–114][211–245], the EGFP gene was deleted from plasmid p[95–114]EGFP[206–245] so that the 35 amino acid long sequence of the dengue virus M protein (DEN-1 virus strain FGA/89, residues 211–245) was directly fused in frame to the C-terminus of the 15 amino acid long sequence of the C protein (DEN-1 virus strain BR/90, residues 95–114) as shown in FIG. 7.

"Consisting essentially of", in relation to amino acid sequence of a protein or peptide, is a term used hereinafter for the purposes of the specification and claims to refer to a conservative substitution or modification of one or more amino acids in that sequence such that the tertiary configuration of the protein or peptide is substantially unchanged.

"Conservative substitutions" is defined by aforementioned function, and includes substitutions of amino acids having substantially the same charge, size, hydrophilicity, and/or aromaticity as the amino acid replaced. Such substitutions, known to those of ordinary skill in the art, include glycine-alanine-valine; isoleucine-leucine; tryptophan-tyrosine; aspartic acid-glutamic acid; arginine-lysine; asparagine-glutamine; and serine-threonine.

"Modification", in relation to amino acid sequence of a protein or peptide, is defined functionally as a deletion of one or more amino acids which does not impart a change in the conformation, and hence the biological activity, of the protein or peptide sequence.

"Consisting essentially of", in relation to a nucleic acid sequence, is a term used hereinafter for the purposes of the specification and claims to refer to substitution of nucleotides as related to third base degeneracy. As appreciated by those skilled in the art, because of third base degeneracy, almost every amino acid can be represented by more than one triplet codon in a coding nucleotide sequence. Further, minor base pair changes may result in variation (conservative substitution) in the amino acid sequence encoded, are not expected to substantially alter the biological activity of the gene product. Thus, a nucleic acid sequencing encoding a protein or peptide as disclosed herein, may be modified slightly in sequence (e.g., substitution of a nucleotide in a triplet codon), and yet still encode its respective gene product of the same amino acid sequence.

The term "expression vector" refers to an oligonucleotide which encodes the peptide of the invention and provides the sequences necessary for its expression in the selected host cell. Expression vectors will generally include a transcriptional promoter and terminator, or will provide for incorporation adjacent to an endogenous promoter. Expression vectors will usually be plasmids, further comprising an origin of replication and one or more selectable markers. However, expression vectors may alternatively be viral recombinants designed to infect the host, or integrating vectors designed to integrate at a preferred site within the host's genome. Examples of viral recombinants are Adeno-associated virus (AAV), Adenovirus, Herpesvirus, Poxvirus, Retrovirus, and other RNA or DNA viral expression vectors known in the art. Examples of other expression vectors are disclosed in *Molecular Cloning: A Laboratory Manual*, Second Edition, Sambrook, Fritsch, and Maniatis, Cold Spring Harbor Laboratory Press, 1989.

Since its amino acid sequence has been disclosed by the present invention, the peptide of the present invention can be produced by a known chemical synthesis method (see, for example, a liquid phase synthesis method, a solid phase synthesis method, etc.; Izumiya, N., Kato, T., Aoyagi, H., Waki, M., "Basis and Experiments of Peptide Synthesis", 1985, Maruzen Co., Ltd.) based on that sequence.

The peptide of the present invention may contain one or more protected amino acid residues. The protected amino acid is an amino acid whose functional group or groups is/are protected with a protecting group or groups by a known method and various protected amino acids are commercially available.

It is preferred that each protective group be selected appropriately from those known per se depending on the conditions of peptide synthesis.

The binding of the protected amino acid is achieved by usual condensation methods, for example, a DCC (dicyclohexylcarbodiimide) method, a DIPCDI (diisopropylcarbodiimide) method (Tartar, A., et al.; J. Org. Chem., 44, 5000 (1979)), an activated ester method, a mixed or symmetric acid anhydride method, a carbonyldiimidazole method, a DCC-HONSu (N-hydroxysuccinimide) method (Weygand, F., et al., Z. Naturforsch., B, 21, 426 (1966)), a DCC-HOBt (1-hydroxybenzotriazole) method (Koenig, W., et al.; Chem. Ber., 103, 788, 2024, 2034 (1970)), a diphenylphosphorylazide method, a BOP-HOBt method (Hudson, D., J. Org. Chem., 53, 617 (1988)) using a BOP reagent (benzotriazolyl-N-hydroxytrisdimethylaminophosphonium hexafluorophosphide), a HBTU (2-(1H-benzotriazol-1-yl)-1,1,3,3-tetramethyluronium hexafluorophosphate)-HOBt method (Knorr, R., et al., Tetrahedron Lett., 30, 1927 (1989)), a TBTU (2-(1H-benzotriazol-1-yl)-1,1,3,3-tetramethyluronium tetrafluoroborate)-HOBt method (Knorr, R., et al., Tetrahedron Lett., 30, 1927 (1989)), etc. However, among these methods, preferred are the DCC method, the DCC-HOBt method, the BOP-HOBt method, the HBTU-HOBt method, and the symmetric acid anhydride method.

The condensation reaction is usually carried out in an organic solvent such as dichloromethane, dimethylformamide (DMF), N-methylpyrrolidone (NMP) and the like or a mixed solvent composed of them.

As the eliminating reagent for the protective group of α-amino group, there can be used trifluoroacetic acid/dichloromethane, HCl/dioxane, piperidine/DMF or piperidine/NMP, etc. and these are selected appropriately depending on the kind of the protecting group.

The degree of progress of condensation reaction in each stage of synthesis can be examined by the method of E. Kaiser, et al. [Anal. Biochem., 34, 595 (1970)] (ninhydrin reaction).

As described above, a protected peptide resin having a desired amino acid sequence can be obtained.

Treatment of the protected peptide resin with hydrogen fluoride, TFMSA (trifluoromethanesulfonic acid) [E. Gross ed., Yajima, H., et al.; "The Peptide" 5, 65 (1983), Academic Press], TMSOTf (trimethylsilyl triflate [Fujii, N., et al.; J. Chem. Soc., Chem. Commun., 274 (1987)], TMSBr (trimethylsilylbromide [Fujii, N., et al.; Chem. Pharm. Bull., 35, 3880 (1987)], trifluoroacetic acid, or the like can eliminate the resin and protecting group simultaneously. The above-described eliminating reagent is selected appropriately depending on the strategy used (Boc or Fmoc) and the kinds of the resin and the protecting group. The peptide of the present invention can be produced by a series of the methods described above.

Alternatively, the peptide of the present invention can be produced by producing a polynucleotide (DNA or RNA) which corresponds to the amino acid sequence of the peptide of the present invention and producing a peptide by a genetic engineering technique using the polynucleotide. Polynucleotide coding sequences for amino acid residues are known in the art and are disclosed for example in *Molecular Cloning: A Laboratory Manual, Second Edition*, Sambrook, Fritsch, and Maniatis, Cold Spring Harbor Laboratory Press, 1989.

The peptide of the present invention thus produced can be purified by isolation/purification methods for proteins generally known in the field of protein chemistry. More particularly, there can be mentioned, for example, extraction, recrystallization, salting out with ammonium sulfate, sodium sulfate, etc., centrifugation, dialysis, ultrafiltration, adsorption chromatography, ion exchange chromatography, hydrophobic chromatography, normal phase chromatography, reversed-phase chromatography, gel filtration method, gel permeation chromatography, affinity chromatography, electrophoresis, countercurrent distribution, etc. and combinations of these.

The peptide of the present invention which is produced can be hydrolyzed with an acid, for example, hydrochloric acid, methanesulfonic acid or the like and its amino acid composition can be examined by a known method. By this, it can be presumed whether or not the peptide of the present invention is produced correctly.

More strictly, the amino acid sequence of the produced peptide is determined by a known amino acid sequence determination method (for example, Edman degradation technique, etc.) to confirm whether the peptide of the present invention is produced correctly.

The peptide of the present invention includes a form of a salt thereof. As described later on, the peptide of the present invention is particularly useful as a medicine and hence the salt of the peptide is preferably a pharmaceutically acceptable salt.

The peptide of the present invention may form a salt by addition of an acid. Examples of the acid include inorganic acids (such as hydrochloric acid, hydrobromic acid, phosphoric acid, nitric acid, and sulfuric acid) or organic carboxylic acids (such as acetic acid, propionic acid, maleic acid, succinic acid, malic acid, citric acid, tartaric acid, and salicylic acid), acidic sugars such as glucuronic acid, galacturonic acid, gluconic acid, ascorbic acid, etc., acidic polysaccharides such as hyaluronic acid, chondroitin sulfates, alginic acid, or organic sulfonic acids (such as methanesulfonic acid, and p-toluenesulfonic acid), and the like. Of these salts, preferred is a pharmaceutically acceptable salt.

The peptide of the present invention may form a salt with a basic substance. Examples of the salt include, for example, pharmaceutically acceptable salts selected from salts with inorganic bases such as alkali metal salts (sodium salt, lithium salt, potassium salt, etc.), alkaline earth metal salts, ammonium salts, and the like or salts with organic bases, such as diethanolamine salts, cyclohexylamine salts, and the like.

The pharmaceutically acceptable carrier which can be used in the present invention is not limited particularly and includes an excipient, a binder, a lubricant, a colorant, a disintegrant, a buffer, an isotonic agent, a preservative, an anesthetic, and the like which can be used in a medical field.

The medicine of the present invention can be applied by any suitable administration method depending on the purpose of treatment and selected from injection (subcutaneous, intracutaneous, intravenous, intraperitoneal, etc.), eye dropping, instillation, percutaneous administration, oral administration, inhalation, and the like.

Also, the dosage form such as injectable preparations (solutions, suspensions, emulsions, solids to be dissolved when used, etc.), tablets, capsules, granules, powders, liquids, liposome inclusions, ointments, gels, external powders, sprays, inhalating powders, eye drops, eye ointments, suppositories, pessaries, and the like can be selected appropriately depending on the administration method, and the peptide of the present invention can be accordingly formulated. Formulation in general is described in Chapter 25.2 of Comprehensive Medicinal Chemistry, Volume 5, Editor Hansch et al, Pergamon Press 1990.

The dose of the medicine of the present invention should be set up individually depending on the purpose of administration (prevention, maintenance (prevention of aggravation), alleviation (improvement of symptom) or cure); the kind of disease; the symptom, sexuality and age of patient; the administration method and the like and is not limited particularly.

The polypeptide and polynucleotide encoding the polypeptide included in these pharmaceutical formulations or medicines may be useful for treating patients infected with members of the Flavivirus genre.

Furthermore, the induction of apoptosis by the pro-apoptotic fragment may be useful for treating patients with cancer. In particular, by specifically targeting cancer cells and inducing apoptosis in those cancer cells. Included in the present invention are the monoclonal antibodies raised against DEN-1 and DEN-2 viral M proteins and their utilization for prevention of disease and diagnostic purposes.

Included in this invention are methods of screening for molecules capable of inducing apoptosis. In particular, the molecules are proteins. This method can be accomplished by attaching the protein to be screened to amino acids 95–114 of the C-protein of Dengue virus; introducing the fusion protein into a cell; and detecting the presence or absence of apoptosis. This method can also be performed by introducing the polypeptide containing the protein to be screened to amino acids 95–114 of the C-protein of Dengue virus directly to the cell.

Polynucleotides may be introduced by a number of well-known methods in the art. Examples of which are Calcium phosphate, DEAE-Dextran, liposomes, viral vectors, etc. These and other methods of introducing polynucleotides into cells are disclosed in Sambrook et al., Molecular Cloning: A Laboratory Manual, Cold Spring Harbor Laboratory, New York (1989).

The present invention further includes methods for screening for molecules which inhibit the cytotoxic activity of the pro-apoptotic fragment of the Dengue virus M protein. This method includes introducing the polypeptide or a polynucleotide encoding the polypeptide into a cell, contacting the cell with the molecule to be screened and detecting the presence or absence of apoptosis. Molecules to be screened can be proteins or any other organic or inorganic substance which may be found to inhibit apoptosis mediated by the amino-terminal 40 amino acids of the Dengue virus M protein.

Antibodies which react specifically with the inventive peptides are also included in the present invention. Methods of generating antibodies directed to a specific peptide fragment are known in the art. Examples of such methods are disclosed in Antibodies, A Laboratory Manual, Harlow and Lane, Cold Spring Harbor Press, 1988, herein incorporated by reference.

Methods of detecting apoptosis include the TUNEL assay and ELISA assay. These and other methods are disclosed in Tomei, L. D. and Cope, F. O. Apoptosis: The Molecular Basis of Cell Death (1991) Cold Spring Harbor Press, N.Y.; Tomei, L. D. and Cope, F. O. Apoptosis II: The Molecular Basis of Apoptosis in Disease (1994) Cold Spring Harbor Press, N.Y.; Duvall and Wyllie (1986) Immun. Today 7(4):115–119 and Sambrook et al., Molecular Cloning: A Laboratory Manual, Cold Spring Harbor Laboratory, New York (1989).

Having generally described this invention, a further understanding can be obtained by reference to certain specific examples which are provided herein for purposes of illustration only, and are not intended to be limiting unless otherwise specified.

EXAMPLES

1. Cells

The Neuro 2a murine neuroblastoma cell line (ATCC Ref. CCL131) was cultured in minimum essential medium (MEM) supplemented with 10% fetal bovine serum (FBS) heat-inactivated for 30 minutes at 56° C. and with nonessential amino acids. The cells were cultured at 37° C. under $CO_2$ on the basis of $10^4$ cells per $cm^2$.

The human hepatoma cell line (ATCC Ref HB8065) was cultured in Eagle medium modified by Dulbecco (D-MEM) supplemented with 10% FBS heat-inactivated for 30 minutes at 56° C., with 4 mM of glutamine and with antibiotics (mixture of penicillin and streptomycin). The cells were cultured at 37° C. under $CO_2$ on the basis of $5\times10^4$ cells per $cm^2$.

2. Plasmids and Transfectant Agent

In order to identify potential pro-apoptotic sequences in prM and E, we constructed the chimeric proteins known as Enhanced Green Fluorescent Protein (EGFP)/DEN. Amino acids 95 to 114 of the C-terminus of the C protein of the DEN-1 virus strain BR/90 function as a signal sequence for translocation of protein prM into ER. This viral signal protein was fused in phase at the N-terminus of the EGFP protein expressed by the pEGFP-N1 expression vector (Clontech #6085-1) to produce the chimeric protein [95–114]EGFP fusion protein (FIG. 2). The peptide segments corresponding to the a helices and to the transmembrane domains of the prM and E glycoproteins were fused in phase at the C-terminus of the chimeric protein [95–114] EGFP (see FIG. 1).

The Neuro 2a and HepG2 cells were transfected by different plasmids recombined by means of FuGENE™ 6 (Roche Molecular Biochemicals #1 814 443) according to the recommended protocol of the commercial kit.

3. TUNEL Detection

During cell death by apoptosis, the genomic DNA is cleaved by activated cellular endonucleases, thus liberating oligonucleosomes. The TUNEL technique permits the oligonucleosomes to be labeled at their free 3'-OH end with modified nucleotides by means of enzyme reaction.

TUNEL-POD labeling was achieved by means of the "In Situ Cell Death Detection" kit (Roche Molecular Biochemicals #1 684 817). The transfected Neuro 2a and HepG2 cells were treated according to the recommended protocol of the commercial kit.

For TUNEL-Cy3 labeling, the Neuro 2a and HepG2 cells transfected for 25 hours were fixed in 3% (w/v) paraformaldehyde (PFA) in PBS. The cells were permeabilized in ethanol then rehydrated in $H_2O$. The cells were then incubated for 15 minutes at 37° C. in the reaction mixture containing 12.5 units of terminal transferase (Roche Molecular Biochemicals #220 582), 2.5 nmol of biotin-16-dUTP (Roche Molecular Biochemicals #1 093 070), 2.5 mM of $CoCl_2$ 0.2 M of potassium cacodylate, 25 mM of TrisCl and 0.25 mg/ml of bovine serum albumin (BSA). The reaction was stopped by incubation for 15 minutes at room temperature in 2× sodium citrate buffer. The cells were washed in $H_2O$ between the different stages. To limit non-specific fixations, the cells were treated with 20 mg/ml of BSA in $H_2O$. The cells were then labeled for 30 minutes at 37° C. using streptavidine conjugated with fluorochrome Cy™ 3 (Jackson ImmunoResearch Laboratories, Inc., #016-160-084). The tests were observed by confocal microscopy.

4. ELISA

When apoptotic death is induced in a cell, cellular endonucleases are activated, and cleave the genomic DNA into oligonucleosomes, The ELISA technique permits quantification of the oligonucleosomes by use of monoclonal antibodies directed against the histones and DNA.

ELISA was performed with the "Cell Death Detection ELISA$^{PLUS}$" kit (Roche Molecular Biochemicals #1 774 425). The transfected Neuro 2a and HepG2 cells were treated according to the recommended protocol of the commercial kit.

5. Staining with Propidium Iodide

During the apoptotic process, the cell undergoes several characteristic morphological modifications. The cell condenses and separates into apoptotic bodies containing DNA fragments. Propidium iodide is a fluorescent agent which becomes inserted between nucleic acids: it permits visual detection of the apoptotic bodies. A cell undergoing apoptosis is defined by the presence of at least three nuclear bodies.

After 20 hours of transfection, the Neuro 2a and HepG2 cells were fixed in 3% (w/v) paraformaldehyde (PFA) in PBS (Table 1). The cells were washed in PBS between the different stages. The cells were treated with 50 mM $NH_4Cl$ in PBS for 10 minutes in order to neutralize the acid vesicles of the trans-Golgi complex, then permeabilized in 0.1% Triton X-100 in PBS for 4 minutes. Degradation of the RNAs was achieved by treatment with 10 μg/ml DNase-free RNase in PBS for 30 minutes at 37° C. The cells were then stained with 1 μg/ml propidium iodide (PI) in 0.1% citrate buffer of pH 6.0. The tests were then observed by fluorescence microscopy.

Figure 3:
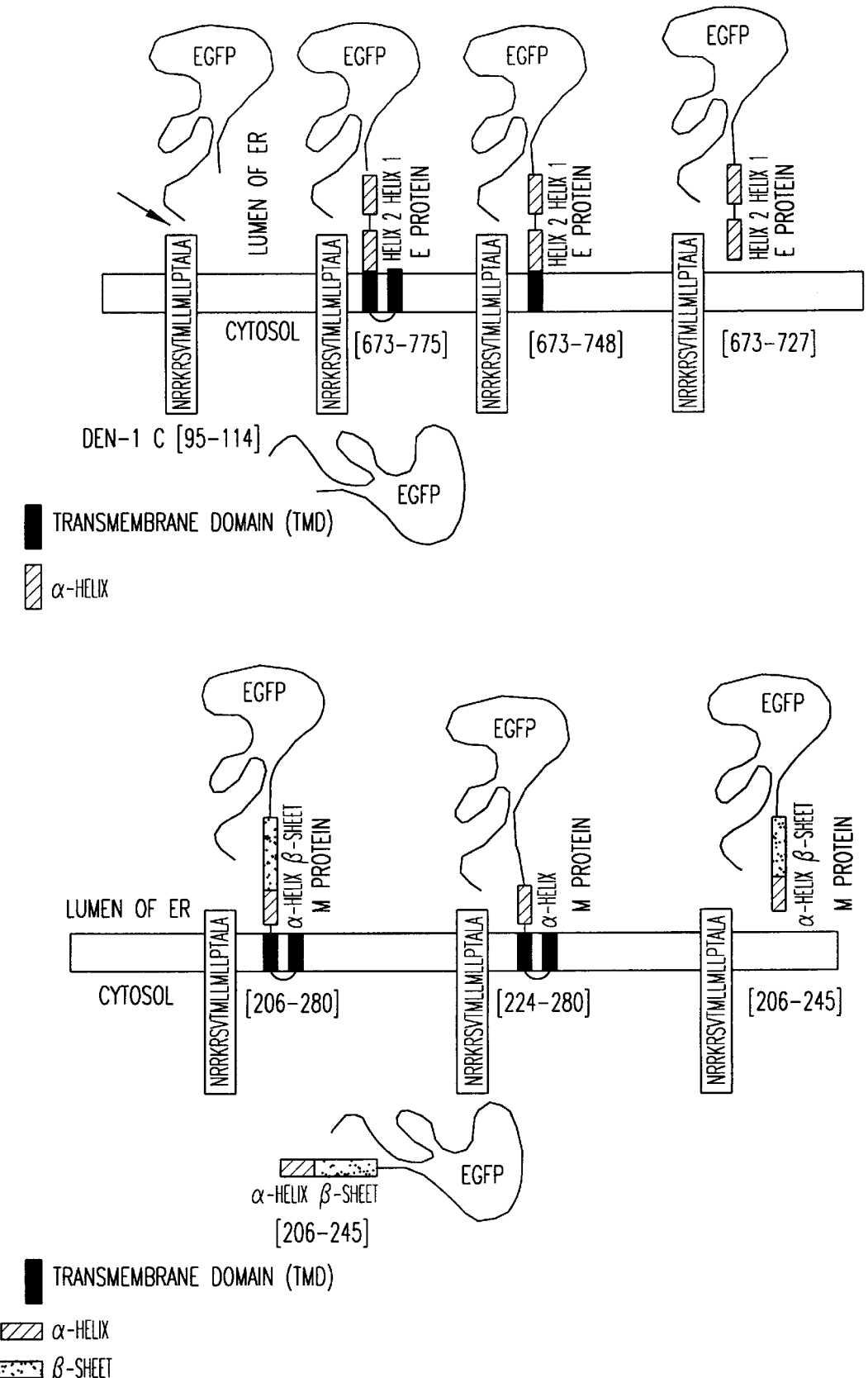
Figure 4A:
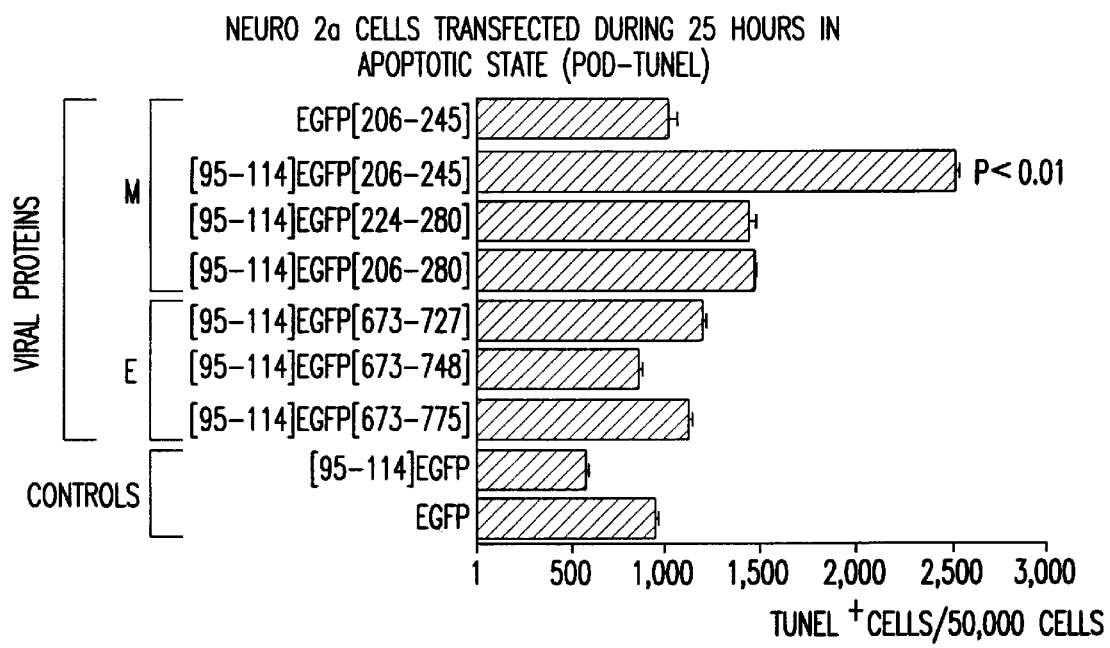
Figure 4B:
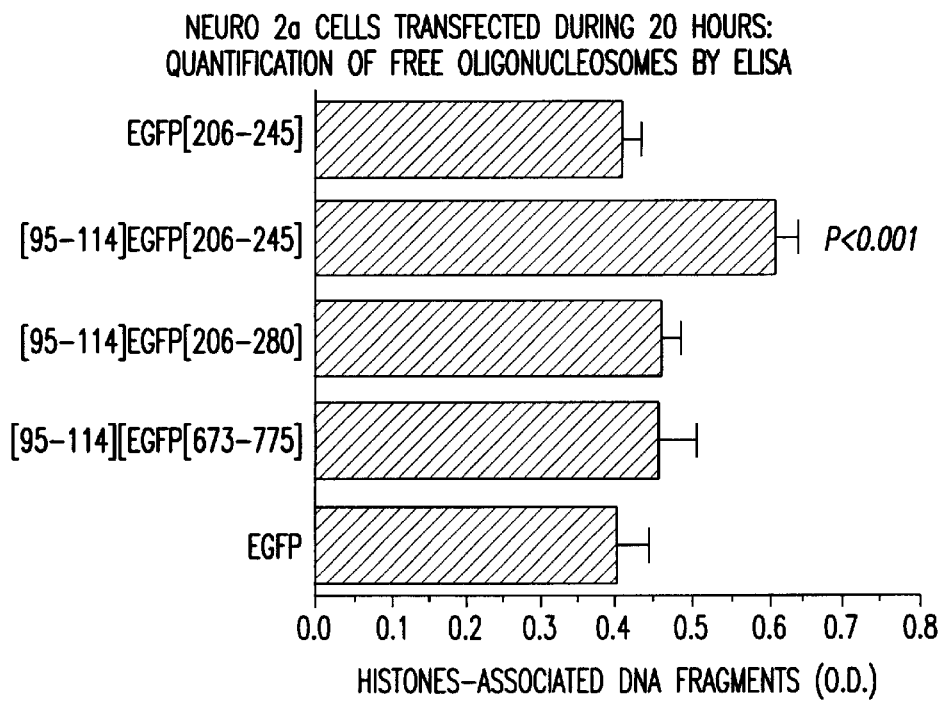
Figure 4C:
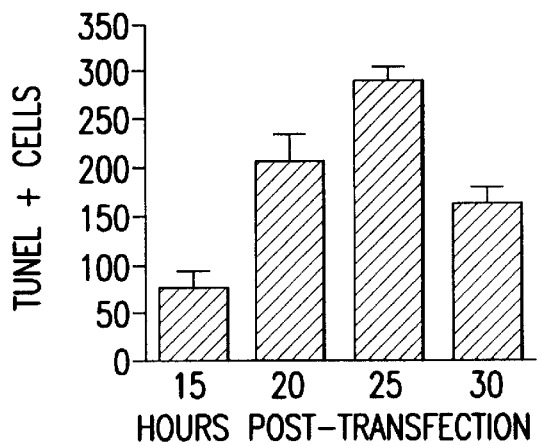
Figure 5A:
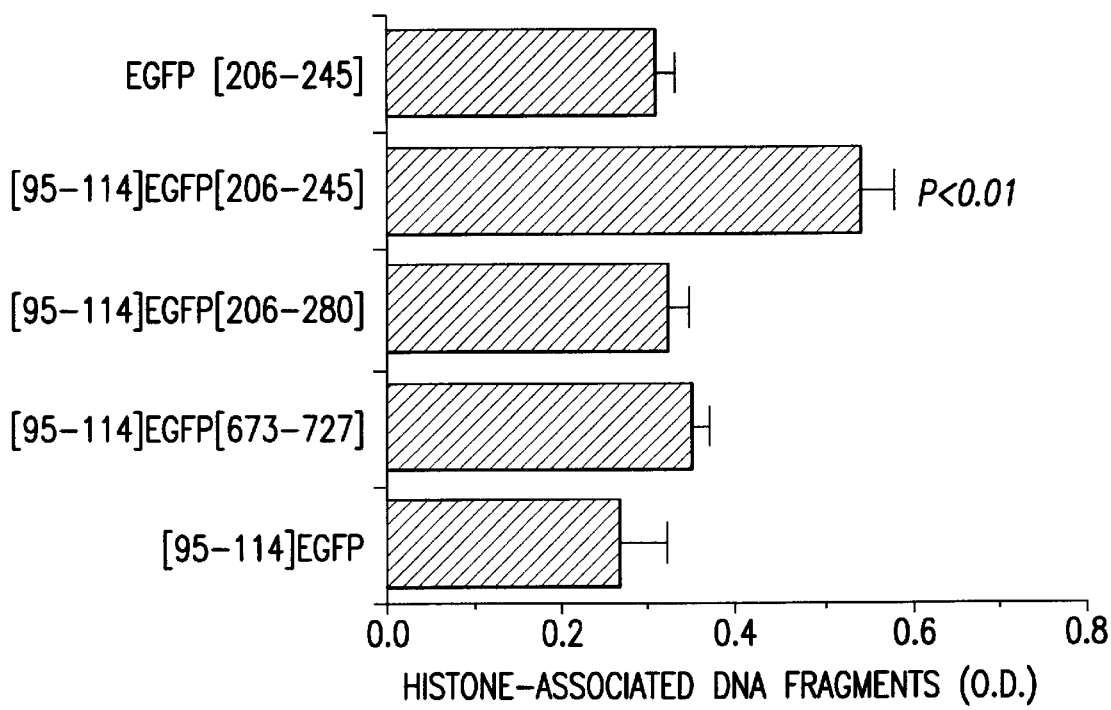
Figure 4D:
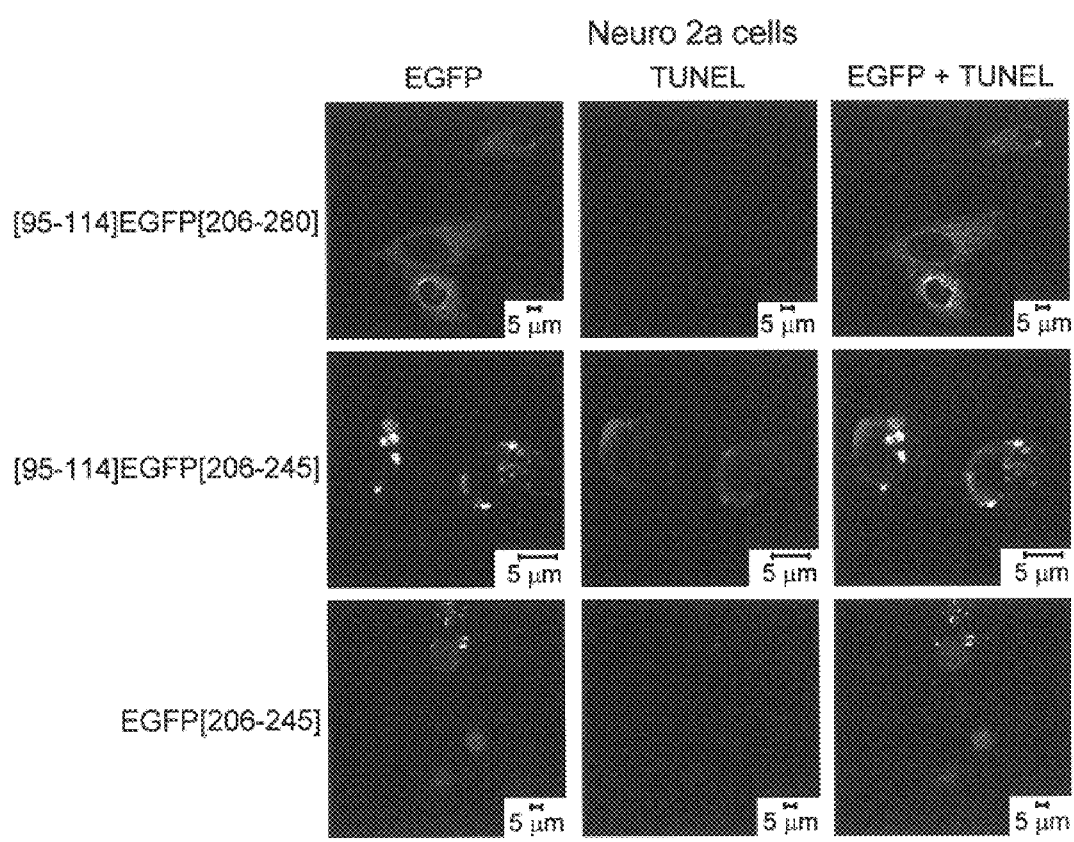
Figure 5B:
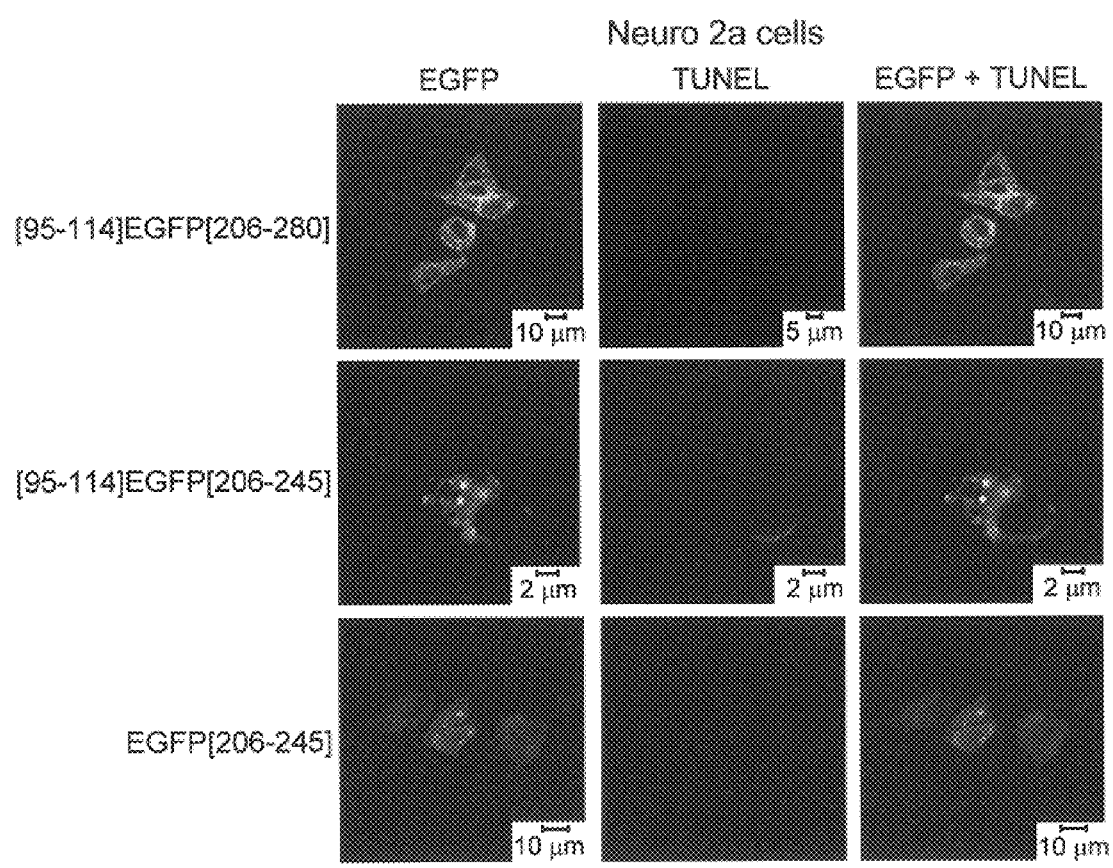
Figure 8:
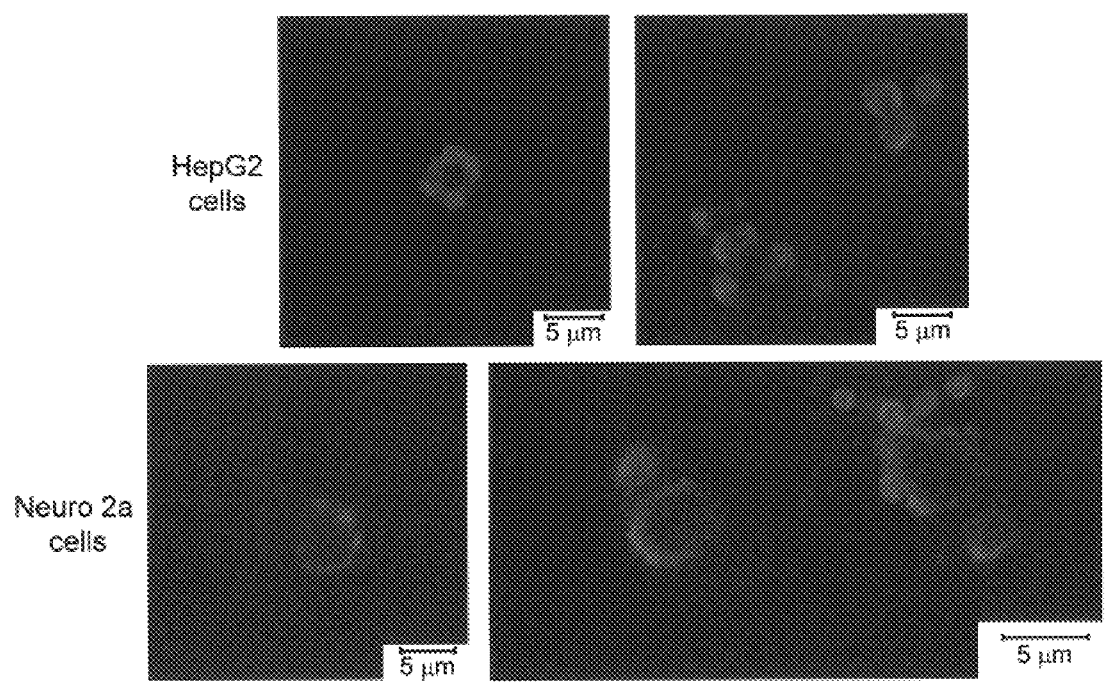

In order to identify potential pro-apoptotic sequences in prM and E, the inventors have constructed chimeric proteins in the form of Enhanced Green Fluorescent Protein (EGFP/DEN). The C-terminal 20 amino acids of the BR/90 C protein (residues 95 to 114) function as a sequence signal to direct the translocation of prM into the lumen of the ER. The two residues alanine at the positions C-112 and C-114 provide a functional signal peptidase site. The C residues 95 to 114 followed by 6 vector-specified amino acids fused to the N-terminus of EGFP encoded by the plasmid pEGFP-N1 (Clontech, #6085-1) produce the [95–114]EGFP fusion protein. The regions of the FGA/89 polyprotein corresponding either the M protein (or its deletion variants) or the predicted c-helices and TMDs of the E protein were fused to the C-terminus of the [95–114]EGFP fusion construct (FIG. 3).

Figure 7:
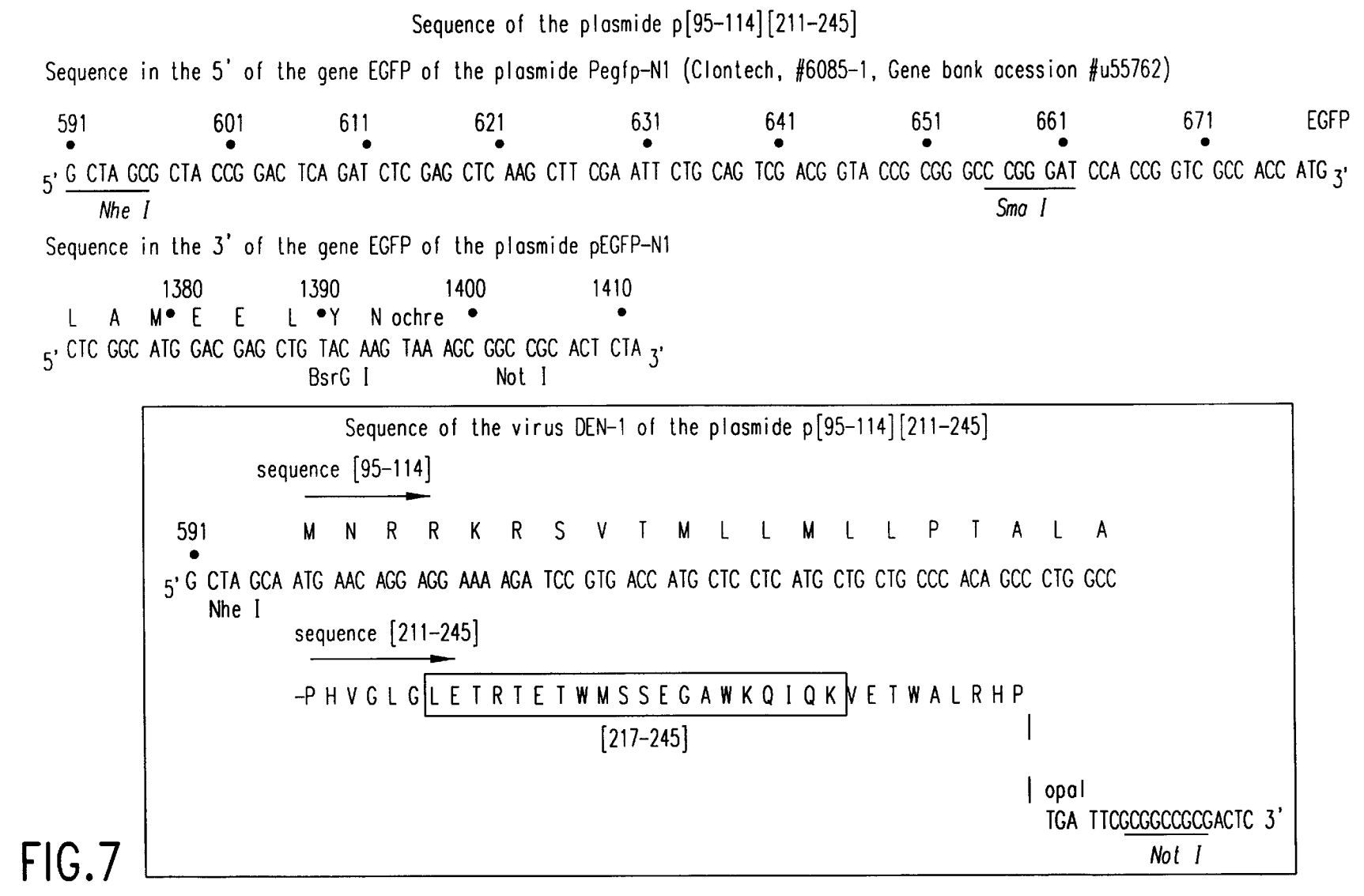

To produce p[95–114][211–245], the EGFP gene was deleted from plasmid p[95–114]EGFP[206–245] so that the 35 amino acid long sequence of the dengue virus M protein (DEN-1 virus strain FGA/89, residues 211–245) was directly fused to the C-terminus of the 15 amino acid long sequence of the C protein (DEN-1 virus strain BR/90, residues 95–114) as it is shown in FIG. 7.

The cytotoxicity of the EGFP/DEN chimeric proteins was tested by transfecting Neuro 2a and HepG2 cells by different plasmids recombined by means of FuGENE™ 6. The expression of different chimeric proteins was observed by the autofluorescence of the EGFP and by radioimmunoprecipitation by means of anti-EGFP antibody. The apoptosis induced by the different chimeric proteins derived from the [95–114] EGFP fusion construct was detected visually by the TUNEL technique and quantified by ELISA, two methods which permit detection of DNA in apoptotic condition (FIGS. 4 and 5).

TABLE 1

| | Neuro 2a cells | | HepG2 cells | |
|---|---|---|---|---|
| | POD-TUNEL[+a] | P[c] | POD-TUNEL[+b] | P |
| [95–114]EGFP [206–280] | 29,85 ± 1,15[d] | | 44,117 ± 2,09 | |
| [95–114]EGFP [206–245] | 59,30 ± 1,00 | <0,01[e] | 66,67 ± 7,88 | <0,02 |
| [95–114][211–245] | 55,50 ± 0,50 | <0,01 | 79,00 ± 8,64 | <0,03 |

[a]Neuro 2a cells are transfected during 22 hours with the [95–114]EGFP [206–280], the [95–114]EGFP[206–245] or the [95–114][211–245] construct. Cells are stained with the POD-TUNEL method, those presented an apoptotic morphology are noted POD-TUNEL+.
[b]HepG2 cells are transfected during 20 hours with the [95–114]EGFP [206–280], the [95–114]EGFP[206–245] or the [95–114][211–245] construct. Cells are stained with the POD-TUNEL method, those presented an apoptotic morphology are noted POD-TUNEL+.
[c]Fisher and Yates t test, comparison of two averages.
[d]POD-TUNEL+ cells are counted of 5000 cells and expressed as the average of two distinct assays.
[e]Datatwere compared to values of 95–114]EGFP[206–280] assays. P < 0,05 was considered significant.

The cytotoxicity of the EGFP/WN chimeric proteins were tested by transfecting Neuro 2a and HepG2 cells with the plasmid [95–114]EGFP[215–255]WNV (deposited at the CNCM under the deposit number I-2485 on May 31, 200) (FIG. 9).

TABLE 2

| | Neuro 2a cells | | HepG2 cells | |
|---|---|---|---|---|
| | POD-TUNEL[+a] | P[c] | POD-TUNEL[+b] | P |
| [95–114]EGFP [206–280] | 160.0 ± 3.0[d] | | 107.0 ± 0.0[d] | |
| [95–114]EGFP [206–245] | 338.0 ± 25.0 | <0,02[e] | 218.0 ± 15.0 | <0,02 |
| [95–114]EGFP [211–255]$_{WNV}$ | 148.0 ± 5.0 | n.s. | 96.5 ± 16.5 | n.s. |

[a]Neuro 2a cells are transfected during 22 hours with the [95–114]EGFP [206–280], the [95–114]EGFP[206–245] or the [95–114]EGFP[211–255]$_{WNV}$ construct. Cells are stained with the PI method, those presented an apoptotic morphology are noted PI+.
[b]HepG2 cells are transfected during 20 hours with the [95–114]EGFP [206–280], the [95–114]EGFP[206–245] or the [95–114]EGFP[211–255]$_{WNV}$ construct. Cells are stained with the POD-TUNEL method, those presented an apoptotic morphology are noted POD-TUNEL+.
[c]Fisher and Yates t test, comparison of two averages.
[d]PI+ or POD-TUNEL+ cells are counted of 50,000 cells and expressed as the average of two distinct assays.
[e]Data were compared to the values of [95–114]EGFP[206–280] assays. P < 0.05 was considered significant. n.s., not significant.

Transient expression analysis with a series of DEN-EGFP fusion constructs revealed that only the construct in which the amino-terminal 40 amino acids of the M protein (DEN polyprotein residues 211 to 245) is fused to the C-terminus of the [95–114]EGFP, significantly induces apoptosis in Neuro 2a and HepG2 cells as early as 20 hours post-transfection. Similar to what has been found for [95–114] EGFP[206–245], transient-expression with the [95–114] [211–245] fusion constructs involving the deletion of the EGFP triggers apoptosis efficiently. Since the proteosome inhibitor (PSI, Calbiochem #539160) delays apoptosis in Neuro 2a cells transfected with plasmid p[95–114]EGFP [206–245], it is presumed that ubiquitin system contributes to cell death process.

It is expected that the 20 amino acid long sequence LETRTETWMSSEGAWKQIQIK of the M protein (amino acids 48–68 of SEQ ID NO:1) (FGA/89 polyprotein residues 217–236) bears significant homology with a region of the Bcl-2 protein family which includes pro-apoptotic proteins such as Bax, since [144–165]Bax versus the M sequence has 23% identity and 64% similarity. The [144–165]Bax region contains the Bcl-2 Homology domain number 2, termed BH2. (Swissprot access:Q07812).

It is expected that the N-terminal 39 amino acids SVALAPHVHLHLETRTETWMSSEGAWKQIQKVETWALRH of the M protein (SEQ ID NO;30) (FGA/89 polyprotein residues 206–244) share 40% identity with the 50 amino acid long sequence (residues 46 to 95) in the cytosolic domain (residues 1 to 95) at the N-terminus of B-CELL DIFFERENTIATION ANTIGEN LYB-2 (CD72), a type II membrane protein. (Swissprot access: P21855).

Plasmid p[95–114]EGFP[206–245]DEN-2

PCR products were prepared from DEN-2 genomic RNA using Expand Reverse Transcriptase and the Expand High Fidelity PCR system (Roche Molecular Biochemicals, Inc.). Oligonucleotide primers including the recognition sites for restriction enzymes BsrGI and NotI, were used to amplify the specific sequence of the DEN-2 RNA encoding the entire M protein. The DEN-2 virus strain Jamaica (Deubel et al., Virology, 196:209–219, 1993) encoding the M protein (DEN-2 polyprotein 206–280) was introduced into BsrGI/NotI-digested p[95–114]EGFP. The resulting plasmid p[95–114]EGFP[206–280]DEN-2 was used as a template to amplify the specific sequence encoding the DEN-2 M ectodomain (DEN-2 polyprotein 206–245) by PCR. The PCR product was cloned in p[95–114]EGFP. The resulting plasmid p[95–114]EGFP[206–245]DEN-2 contains the DEN-2 M ectodomain (DEN-2 polyprotein 206–245) fused in frame to the fusion protein [95–114]EGFP. The sequences were confirmed by automated sequencing. The plasmid p[95–114]EGFP[206–245]DEN-2 has been deposited at the Collection Nationale de Cultures de Microorganismes, 25, rue du Dr Roux, F-75724 Paris Cedex 15 on Jan. 29, 2001 under the number I-2620.

To test the pro-apoptotic activity of the DEN-2 M ectodomain, the inventors employed the chimeric protein [95–114]EGFP[206–245]DEN-2. Amino acids 95–114 of the C-terminus of the C protein of the DEN-1 virus strain BR/90 act as a signal sequence for translocation of protein M into the ER. This viral signal polypeptide was fused in phase to the N-terminus of the EGFP protein expressed by the pEGFP-N1 expression vector (Clontech # 6085-1) to produce the chimeric protein [95–114]EGFP. The region of the DEN-2 virus strain Jamaica corresponding the M ectodomain (DEN-2 polyprotein 206–245) was fused to the C-terminus of the [95–114]EGFP fusion construct. This construct is depicted in FIG. 11.

The cytotoxicity of the [95–114]EGFP[206–245]DEN-2 chimeric protein was tested by transfecting cells with FuGENE™ 6. The expression of the chimeric protein was observed by the autofluorescence of the EGFP and apoptotic cell death was detected visually by staining with propidium iodide as described above. Intracellular expression of the [95–114]EGFP[206–245]DEN-2 chimeric protein resulted in cell death. DEN-2 M ectodomain has the ability to induce rapid apoptosis in Neuro 2a, HepG2, HeLa and VERO cells. Apoptosis was more pronounced after transfection with plasmid p[95–114]EGFP[206–245]DEN-2 than after transfection with the plasmid [95–114]EGFP[206–245] containing the sequence of the DEN-1 M ectodomain.

The inventors also tested the ability of the DEN-1, DEN-2 and WN M ectodomains to induce apoptosis in transiently-transfected human cell lines HeLa (ATCC N° CCL-2), 293T (provided by Pierre Charneau, see his patent on retroviral vector) and the non-human primate cell line VERO (ATCC N° CCL-81; kindly provided by Marie Flamand).

The expression of the EGFP/DEN and EGFP/WN chimeric proteins was observed by the autofluorescence of the EGFP and apoptosis was detected visually by staining with Hoechst or propidium iodide after 25 h of transfection.

The chimeric proteins [95–114]EGFP[206–245]DEN-1 and [95–114]EGFP[206–245]DEN-2 were present in large fluorescent masses in HeLa, 293T and VERO. There was no large fluorescent bodies in transfected cells expressing the chimeric protein [95–114]EGFP[215–255]WN.

Figure 15:
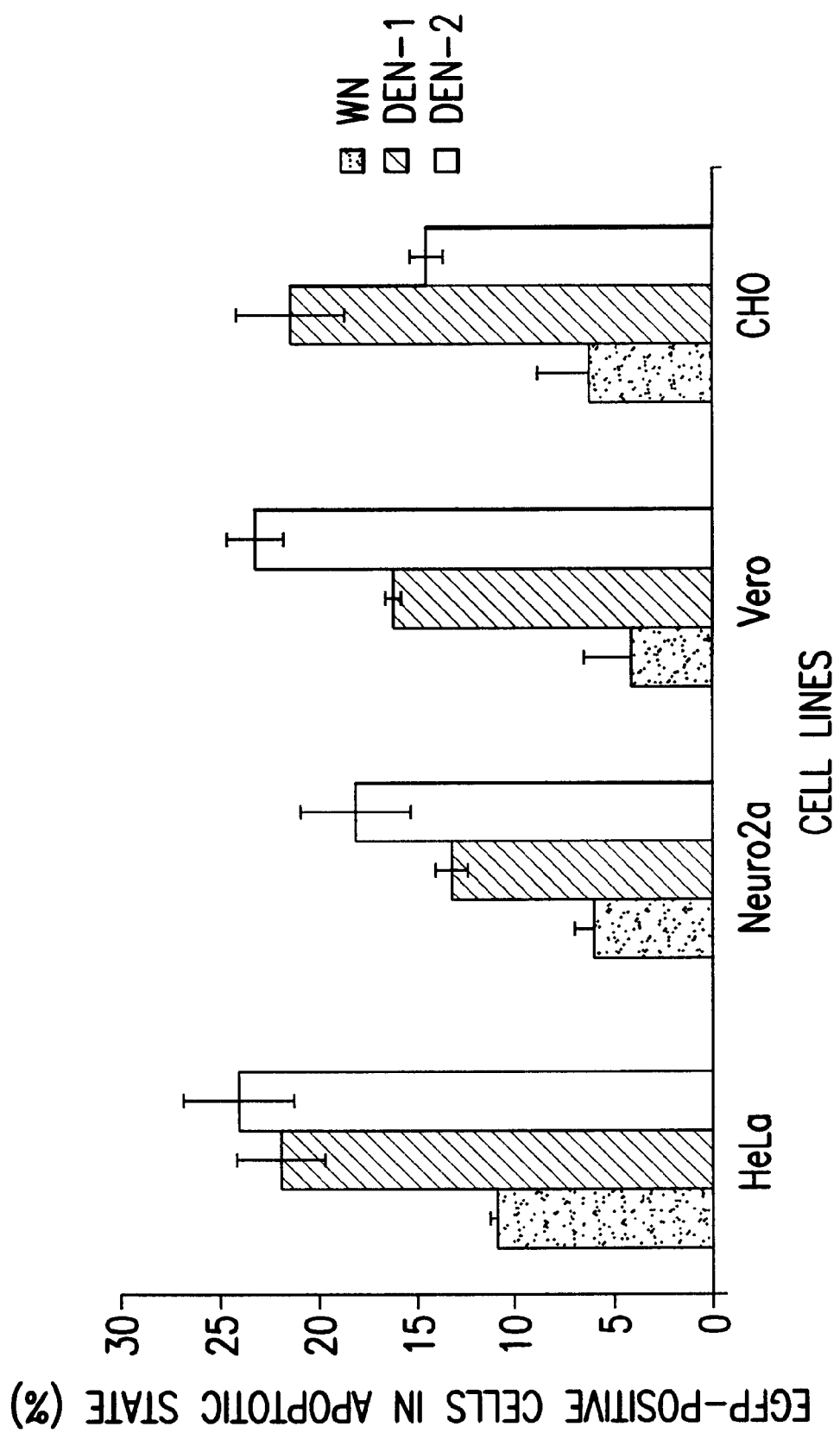

The chimeric proteins [95–114]EGFP[206–245]DEN-1 and [95–114]EGFP[206–245]DEN-2 induced apoptosis in HeLa and VERO cells at 25 h of transfection whereas chimeric protein [95–114]EGFP[215–255]WN did not cause cell death (FIG. 15). Intracellular expression of the chimeric proteins [95–114]EGFP[206–245]DEN-1, [95–114]EGFP[206–245]DEN-2, and [95–114]EGFP [215–255]WN did not induce apoptosis in 293T cells. The chimeric proteins accumulated in transiently-transfected 293T cells after 72 h of transfection. Thus, the 293T cell line is mainly resistant to the death-inducing activity of the DEN M ectodomains. The cell clone 293T was generated by introducing the SV40 T-antigen coding sequence into the human epithelial cell line 293 (ATCC N° CRL-1573) which carries the Adenovirus 5 transforming genes.

Deletion Variants of the DEN-2 M Ectodomain

The inventors also studied elements of the sequence which contribute to the efficient death-inducing activity of the DEN M ectodomain. Variants were constructed in which either the C-terminal region or the N-terminal region of the DEN-2 M ectodomain was removed by PCR deletion mutagenesis.

The deletion variants of the sequence M1→M40 of the DEN-2 ectodomain (SEQ ID NO:29):

```
1         10        20        30        40
SVALVPHVGMGLETRTETWMSSEGAWKHAQRIETWILRHP
``` included either the segment M1→M30 ([95–114]EGFP [M1→M30]DEN-2), the segment M1→M20 ([95–114] EGFP[M1→M20]DEN-2), the segment M1→M40 ([95–114]EGFP[M1→M40]DWN-2), the M20→M40 ([95–114]EGFP[M20→M40]DEN-2), the segment M10→M30 ([95–114]EGFP[M10→M30]DEN-2) or the segment M30→M40 ([95–114]EGFP[M30→M40]DEN-2). The deletion mutants of plasmid p[95–114]EGFP[206–245] DEN-2 are shown in FIG. 12.

The expression of these deletion variants of the DEN-2 M ectodomain was examined by transient transfection of 293T cells. The deletion variants were tested for their ability to cause cell death upon the transfection of HeLa cells. Transiently-transfected cells were analyzed for apoptosis by staining with Hoechst.

Transient expression of the deletion variants of the chimeric protein [95–114]EGFP[206–245]DEN-2 demonstrated that amino acids M10→M40 of the M ectodomain ([95–114]EGFP[M10→M40]DEN-2) significantly contribute to the efficient formation of the fluorescent masses in the secretory pathway (FIG. 12). The death-inducing activity of DEN-2 M ectodomain is also attribuable to the amino acids M10 to M40 (FIG. 12). The plasmid [95–114]EGFP [M10–M40]DEN-2 has been deposited at the Collection Nationale De Cultures De Microorganismes (CNCM), Institut Pasteur, 28, rue du Dr Roux, 75724 Paris Cédex 15, France on Jun. 14, 2001 under the accession number I-2684.

DEN M Ectodomain Tends to Form Reversible Aggregates In vitro

The procaryotic expression vector pIVEX-2.4a (Roche Molecular Biochemicals, Inc.) with T7 promoter was tested for in vitro synthesis of the fusion construct EGFP[206–245] DEN-2. The PCR product was prepared from the plasmid p[95–114]EGFP[206–245]DEN-2 using the Expand High Fidelity PCR system (Roche Molecular Biochemicals, Inc.). Oligonucleotide primers including the recognition sites for restriction enzymes KspI and SmaI, were used to amplify the specific sequence encoding the fusion construct EGFP [206–245]DEN-2 by PCR.

The PCR product was introduced into KspI/SmaI-digested pIVEX-2.4a (Roche Molecular Biochemicals, Inc.) to generate pIVEX-EGFP[206–245]DEN-2. The RTS 500 system (Roche Molecular Biochemicals, Inc.) was used to produce large amount of the chimeric protein EGFP [206–245]DEN-2 tagged with [His]6 by using the plasmid pIVEX-EGFP[206–245]DEN-2 as transcription template.

In vitro, the newly synthesized molecules EGFP [206–245]DEN-2 tend to aggregate as autofluorescent precipitates. The aggregates were solubilized by incubating with 8 M urea, suggesting that the formation of these high-order structures required hydophobic interactions. The inventors have shown that the above expression system is useful to produce ectoM molecules. These molecules are useful to produce antibodies specific of the ectoM molecules according to known protocols of producing antibodies (Harlow and Lane, Antibodies: A Laboratory Manual, Cold Spring Harbor Laboratory Press, Cold Spring Harbor, N.Y., 1988).

Intracellular Expression of DEN M Ectodomain by Transduction

The plasmid pTRIPΔU3CMVEGFP (International Patent Application WO 99/55892, the contents of which are incorporated by reference) was required for intracellular expression of DEN M ectodomains after transduction. The PCR products were prepared either from plasmids p[95–114] EGFP[206–245] which contains DEN-1 M ectodomain or p[95–114]EGFP[206–245]DEN-2 using the Expand High Fidelity PCR system (Roche Molecular Biochemicals, Inc.). Oligonucleotide primers including the recognition sites for restriction enzymes BglII and KpnI, were used to amplify the specific sequences encoding the fusion constructs EGFP/DEN. The PCR products were introduced into BamHI/KpnI-digested pTRIP(U3CMVEGFP.

The resulting plasmids pTRIPΔU3CMV[95–114]EGFP [206–245]DEN-1 and pTRIPΔU3CMV[95–114]EGFP [206–245]DEN-2 were used to generate non-replicative retroviruses carrying the sequences coding for the chimeric proteins EGFP/DEN M ectodomain as described in the International patent application WO 99/55892, (Pierre Charneau's et al.). Large flasks of 293T cell monolayers were co-transfected 2 days with pTRIPΔU3CMV[95–114]EGFP [206–245]DEN-1 or pTRIPΔU3CMV[95–114]EGFP [206–245]DEN-2 and plasmids which carry sequences coding either for VSV envelope G protein or HIV proteins.

The plasmid pTripΔU3[95–114]EGFP[206–265]DEN-2 has been deposited at the Collection Nationale De Cultures De Microorganismes (CNCM), Institut Pasteur, 28, rue du Dr Roux, 75724 Paris Cédex 15, France on Jun. 14, 2001 under the accession number I-2686.

The plasmid pTripΔUS[95–114]EGFP[206–245]DEN-1 has been deposited at the Collection Nationale De Cultures De Microorganismes (CNCM), Institut Pasteur, 28, rue du Dr Roux, 75724 Paris Cédex 15, France on Jun. 14, 2001 under the accession number I-2685.

The production and the purification of recombinant retroviruses were essentially performed as described in the International patent application WO 99/55892, (the contents of which are incorporated herein by reference).

Figure 13:
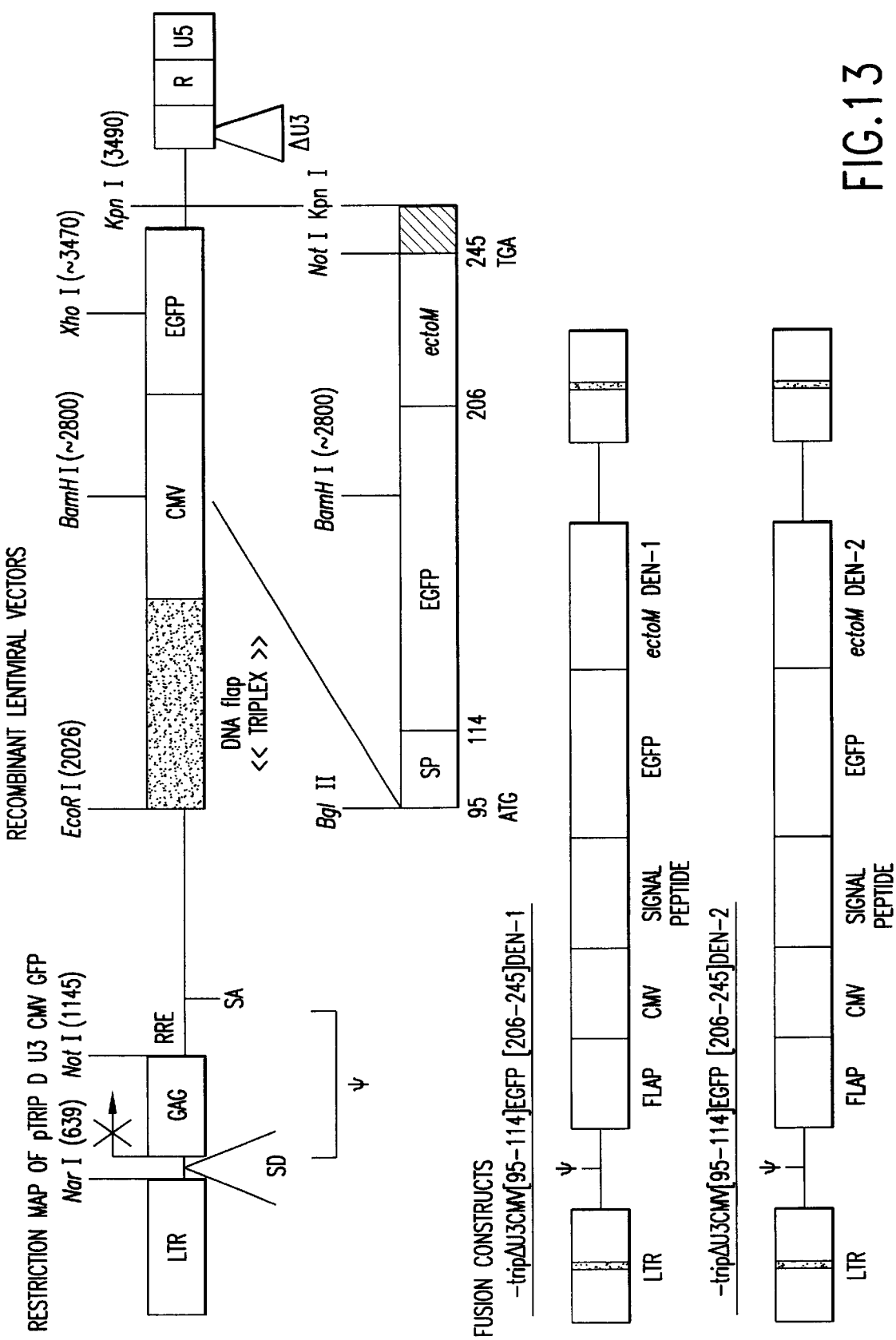
Figure 14:
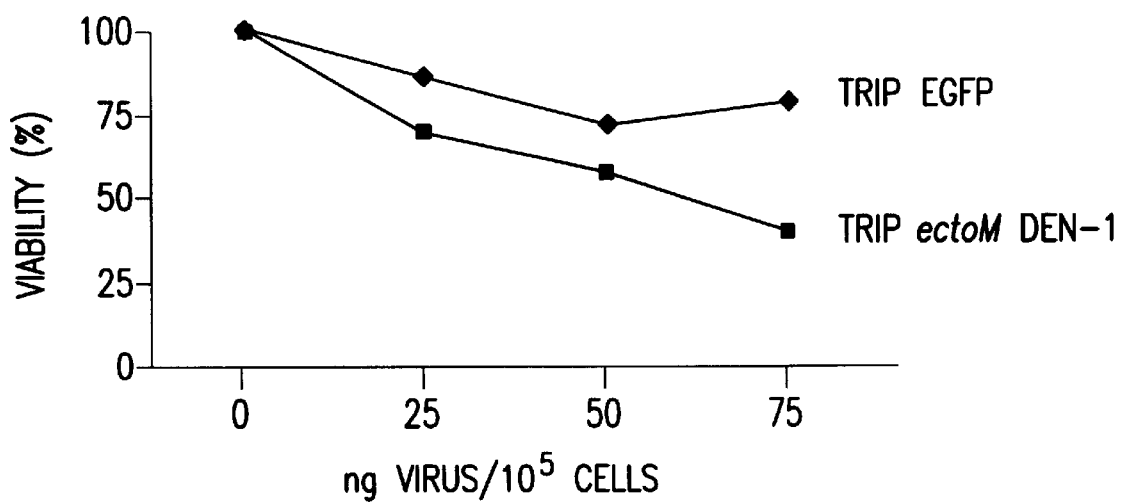

The production of recombinant virus particles pTRIP (U3CMV[95–114]EGFP[206–245]DEN-1 and pTRIP (U3CMV[95–114]EGFP[206–245]DEN-2 was determined in measuring the amount of soluble p24 by ELISA. At dose as low as 1 ng of recombinant retrovirus pTRIP(U3CMV [95–114]EGFP[206–245]DEN-1 per 3.104 cells, more than 80% of 293T cell were positive for EGFP after 48 h of transduction (FIG. 13).

Obviously, numerous modifications and variations on the present invention are possible in light of the above teachings. It is therefore to be understood that within the scope of the appended claims, the invention may be practiced otherwise than as specifically described herein.

What is claimed is:

1. An isolated polypeptide having a sequence according to SEQ ID NO:1.

2. The isolated polypeptide of claim 1, wherein said polypeptide induces apoptosis in a cell.

3. A composition comprising the polypeptide of claim 1 and a physiological acceptable carrier.

4. An isolated polypeptide having a sequence according to SEQ ID NO:2.

5. A composition comprising the polypeptide of claim 4 and a physiological acceptable carrier.

6. An isolated polypeptide having a sequence according to SEQ ID NO: 1 linked to a sequence according to SEQ ID NO:2.

7. A composition comprising the polypeptide of claim 6, and a physiological acceptable carrier.

* * * * *

SEQUENCE LISTING

```
<160> NUMBER OF SEQ ID NOS: 30

<210> SEQ ID NO 1
<211> LENGTH: 76
<212> TYPE: PRT
<213> ORGANISM: Dengue virus

<400> SEQUENCE: 1

Met Asn Arg Arg Lys Arg Ser Val Thr Met Leu Leu Met Leu Leu Pro
1               5                   10                  15

Thr Ala Leu Ala Arg Glu Pro Pro Val Ala Thr Met Leu Ala Met Glu
            20                  25                  30

Glu Leu Tyr Ser Ser Val Ala Leu Ala Pro His Val Gly Leu Gly Leu
        35                  40                  45

Glu Thr Arg Thr Glu Thr Trp Met Ser Ser Glu Gly Ala Trp Lys Gln
    50                  55                  60

Ile Gln Lys Val Glu Thr Trp Ala Leu Arg His Pro
65                  70                  75

<210> SEQ ID NO 2
<211> LENGTH: 20
<212> TYPE: PRT
<213> ORGANISM: Dengue virus

<400> SEQUENCE: 2

Met Asn Arg Arg Lys Arg Ser Val Thr Met Leu Leu Met Leu Leu Pro
1               5                   10                  15
```

-continued

Thr Val Leu Ala
        20

<210> SEQ ID NO 3
<211> LENGTH: 30
<212> TYPE: PRT
<213> ORGANISM: Dengue virus

<400> SEQUENCE: 3

Pro His Val Gly Met Gly Leu Glu Thr Arg Thr Glu Thr Trp Met Ser
1               5                   10                  15

Ser Glu Gly Ala Trp Lys His Val Gln Arg Ile Glu Thr Trp
            20                  25                  30

<210> SEQ ID NO 4
<211> LENGTH: 91
<212> TYPE: DNA
<213> ORGANISM: Dengue virus

<400> SEQUENCE: 4
gctagcgcta ccggactcag atctcgagct caagcttcga attctgcagt cgacggtacc      60
gcgggcccgg gatccaccgg tcgccaccat g                                     91

<210> SEQ ID NO 5
<211> LENGTH: 91
<212> TYPE: DNA
<213> ORGANISM: Dengue virus

<400> SEQUENCE: 5
gctagcaatg aacaggagga aaagatccgt gaccatgctc ctcatgctgc tgcccacagc      60
cctggcccgg gatccaccgg tcgccaccat g                                     91

<210> SEQ ID NO 6
<211> LENGTH: 42
<212> TYPE: DNA
<213> ORGANISM: Dengue virus

<400> SEQUENCE: 6
ctcggcatgg acgagctgta caagtaaagc ggccgcactc ta                         42

<210> SEQ ID NO 7
<211> LENGTH: 73
<212> TYPE: DNA
<213> ORGANISM: Dengue virus

<400> SEQUENCE: 7
ctcggcatgg acgagctgta cagttccgtg gctctggccg ctttgagaca cccatgattc      60
gcggccgcga ctc                                                         73

<210> SEQ ID NO 8
<211> LENGTH: 42
<212> TYPE: DNA
<213> ORGANISM: Dengue virus

<400> SEQUENCE: 8
ctcggcatgg acgagctgta caagtaaagc ggccgcactc ta                         42

<210> SEQ ID NO 9
<211> LENGTH: 8
<212> TYPE: PRT
<213> ORGANISM: Dengue virus

-continued

<400> SEQUENCE: 9

```
Leu Ala Met Glu Glu Leu Tyr Asn
1               5
```

<210> SEQ ID NO 10
<211> LENGTH: 20
<212> TYPE: PRT
<213> ORGANISM: Dengue virus

<400> SEQUENCE: 10

```
Met Asn Arg Arg Lys Arg Ser Val Thr Met Leu Leu Met Leu Leu Pro
1               5                   10                  15

Thr Val Leu Ala
            20
```

<210> SEQ ID NO 11
<211> LENGTH: 30
<212> TYPE: PRT
<213> ORGANISM: Dengue virus

<400> SEQUENCE: 11

```
Pro His Val Gly Met Gly Leu Glu Thr Arg Thr Glu Thr Trp Met Ser
1               5                   10                  15

Ser Glu Gly Ala Trp Lys His Val Gln Arg Ile Glu Thr Trp
            20                  25                  30
```

<210> SEQ ID NO 12
<211> LENGTH: 39
<212> TYPE: PRT
<213> ORGANISM: Dengue virus

<400> SEQUENCE: 12

```
Ser Val Ala Leu Ala Pro His Val Gly Leu Gly Leu Glu Thr Arg Thr
1               5                   10                  15

Glu Thr Trp Met Ser Ser Glu Gly Ala Trp Lys Gln Ile Gln Lys Val
            20                  25                  30

Glu Thr Trp Ala Leu Arg His
        35
```

<210> SEQ ID NO 13
<211> LENGTH: 39
<212> TYPE: PRT
<213> ORGANISM: Mus musculus

<400> SEQUENCE: 13

```
Ser Pro Ala Leu Ala Asp Lys Ala Gly Val Ser Glu Gln Pro Thr Ala
1               5                   10                  15

Thr Trp Ser Ser Val Lys Ser Ser Ala Leu Arg Gln Ile Pro Arg Cys
            20                  25                  30

Pro Thr Val Cys Leu Gln Asn
        35
```

<210> SEQ ID NO 14
<211> LENGTH: 20
<212> TYPE: PRT
<213> ORGANISM: Homo sapiens

<400> SEQUENCE: 14

```
Leu Arg Glu Arg Leu Leu Gly Trp Ile Gln Asp Gln Gly Gly Trp Asp
1               5                   10                  15

Gly Leu Leu Ser
```

20

<210> SEQ ID NO 15
<211> LENGTH: 20
<212> TYPE: PRT
<213> ORGANISM: Dengue virus

<400> SEQUENCE: 15

Leu Glu Thr Arg Thr Glu Thr Trp Met Ser Ser Glu Gly Ala Trp Lys
1               5                   10                  15

His Ala Gln Arg
            20

<210> SEQ ID NO 16
<211> LENGTH: 20
<212> TYPE: PRT
<213> ORGANISM: Dengue virus

<400> SEQUENCE: 16

Leu Asp Thr Arg Thr Gln Thr Trp Met Ser Ala Glu Gly Ala Trp Arg
1               5                   10                  15

Gln Val Glu Lys
            20

<210> SEQ ID NO 17
<211> LENGTH: 20
<212> TYPE: PRT
<213> ORGANISM: Dengue virus

<400> SEQUENCE: 17

Leu Glu Thr Arg Ala Glu Thr Trp Met Ser Ser Glu Gly Ala Trp Lys
1               5                   10                  15

His Ala Gln Arg
            20

<210> SEQ ID NO 18
<211> LENGTH: 20
<212> TYPE: PRT
<213> ORGANISM: Kunjin virus

<400> SEQUENCE: 18

Leu Ser Asn Lys Lys Gly Ala Trp Met Asp Ser Thr Lys Ala Thr Arg
1               5                   10                  15

Tyr Leu Val Lys
            20

<210> SEQ ID NO 19
<211> LENGTH: 20
<212> TYPE: PRT
<213> ORGANISM: Japanese encephalitis virus

<400> SEQUENCE: 19

Leu Val Asn Lys Lys Glu Ala Trp Leu Asp Ser Thr Lys Ala Thr Arg
1               5                   10                  15

Tyr Leu Met Lys
            20

<210> SEQ ID NO 20
<211> LENGTH: 20
<212> TYPE: PRT
<213> ORGANISM: Murray Valley encephalitis virus

<400> SEQUENCE: 20

-continued

Leu Val Asn Lys Lys Asp Ala Trp Leu Asp Ser Thr Lys Ala Thr Arg
1               5                   10                  15

Tyr Leu Thr Lys
            20

<210> SEQ ID NO 21
<211> LENGTH: 20
<212> TYPE: PRT
<213> ORGANISM: West Nile virus

<400> SEQUENCE: 21

Leu Ala Asn Lys Lys Gly Ala Trp Met Asp Ser Thr Lys Ala Thr Arg
1               5                   10                  15

Tyr Leu Val Lys
            20

<210> SEQ ID NO 22
<211> LENGTH: 20
<212> TYPE: PRT
<213> ORGANISM: St. Louis encephalitis virus

<400> SEQUENCE: 22

Leu Ala Thr Lys Asn Thr Pro Trp Leu Asp Thr Val Lys Thr Thr Lys
1               5                   10                  15

Tyr Leu Thr Lys
            20

<210> SEQ ID NO 23
<211> LENGTH: 20
<212> TYPE: PRT
<213> ORGANISM: Vesicular stomatitis virus

<400> SEQUENCE: 23

Leu Lys Thr Arg Gln Glu Lys Trp Met Thr Gly Arg Met Gly Glu Arg
1               5                   10                  15

Gln Leu Gln Lys
            20

<210> SEQ ID NO 24
<211> LENGTH: 20
<212> TYPE: PRT
<213> ORGANISM: Tick-borne encephalitis virus

<400> SEQUENCE: 24

Leu Thr Gly Arg Gly His Lys Trp Leu Glu Gly Asp Ser Leu Arg Thr
1               5                   10                  15

His Leu Thr Arg
            20

<210> SEQ ID NO 25
<211> LENGTH: 20
<212> TYPE: PRT
<213> ORGANISM: Flavivirus langat

<400> SEQUENCE: 25

Leu Thr Gly Arg Gly His Gln Trp Leu Glu Gly Glu Ala Val Lys Ala
1               5                   10                  15

His Leu Thr Arg
            20

<210> SEQ ID NO 26

-continued

```
<211> LENGTH: 20
<212> TYPE: PRT
<213> ORGANISM: Powassan virus

<400> SEQUENCE: 26

Met Val Gly Thr Gly His Ala Trp Leu Lys Gly Asp Asn Ile Arg Asp
1               5                   10                  15

His Val Thr Arg
            20

<210> SEQ ID NO 27
<211> LENGTH: 41
<212> TYPE: PRT
<213> ORGANISM: West Nile virus

<400> SEQUENCE: 27

Arg Ser Leu Thr Val Gln Thr His Gly Glu Ser Thr Leu Ala Asn Lys
1               5                   10                  15
Lys Gly Ala Trp Met Asp Ser Thr Lys Ala Thr Arg Tyr Leu Val Lys
            20                  25                  30
Thr Glu Ser Trp Ile Leu Arg Asn Pro
        35                  40

<210> SEQ ID NO 28
<211> LENGTH: 40
<212> TYPE: PRT
<213> ORGANISM: Dengue virus

<400> SEQUENCE: 28

Ser Val Ala Leu Ala Pro His Val Gly Leu Gly Leu Glu Thr Arg Thr
1               5                   10                  15

Glu Thr Trp Met Ser Ser Glu Gly Ala Trp Lys Gln Ile Gln Lys Val
            20                  25                  30

Glu Thr Trp Ala Leu Arg His Pro
        35                  40

<210> SEQ ID NO 29
<211> LENGTH: 40
<212> TYPE: PRT
<213> ORGANISM: Dengue virus

<400> SEQUENCE: 29

Ser Val Ala Leu Val Pro His Val Gly Met Gly Leu Glu Thr Arg Thr
1               5                   10                  15

Glu Thr Trp Met Ser Ser Glu Gly Ala Trp Lys His Ala Gln Arg Ile
            20                  25                  30

Glu Thr Trp Ala Leu Arg His Pro
        35                  40

<210> SEQ ID NO 30
<211> LENGTH: 39
<212> TYPE: PRT
<213> ORGANISM: Dengue virus

<400> SEQUENCE: 30

Ser Val Ala Leu Ala Pro His Val His Leu His Leu Glu Thr Arg Thr
1               5                   10                  15

Glu Thr Trp Met Ser Ser Glu Gly Ala Trp Lys Gln Ile Gln Lys Val
            20                  25                  30

Glu Thr Trp Ala Leu Arg His
        35
```